(12) United States Patent
Bubenik et al.

(10) Patent No.: US 10,639,430 B2
(45) Date of Patent: May 5, 2020

(54) HINGED SHIELD ASSEMBLIES AND RELATED METHODS

(75) Inventors: Janko Bubenik, Morschen (DE); Harald Heckmann, Lohfelden (DE); Volker Harms, Kassel (DE)

(73) Assignee: B. Braun Melsungen AG, Melsungen (DE)

( * ) Notice: Subject to any disclaimer, the term of this patent is extended or adjusted under 35 U.S.C. 154(b) by 277 days.

(21) Appl. No.: 13/878,305

(22) PCT Filed: Nov. 22, 2011

(86) PCT No.: PCT/US2011/061825
§ 371 (c)(1),
(2), (4) Date: May 20, 2013

(87) PCT Pub. No.: WO2012/071400
PCT Pub. Date: May 31, 2012

(65) Prior Publication Data
US 2013/0274684 A1    Oct. 17, 2013

Related U.S. Application Data

(60) Provisional application No. 61/416,257, filed on Nov. 22, 2010.

(51) Int. Cl.
*A61M 5/32* (2006.01)

(52) U.S. Cl.
CPC ........ *A61M 5/3216* (2013.01); *A61M 5/3202* (2013.01); *A61M 5/3205* (2013.01); *A61M 5/3219* (2013.01); *A61M 2005/3206* (2013.01)

(58) Field of Classification Search
CPC .............. A61M 5/1626; A61M 5/3202; A61M 5/3205; A61M 5/321; A61M 5/3216;
(Continued)

(56) References Cited

U.S. PATENT DOCUMENTS 3,841,769 A * 10/1974 Bowerman ............... B60R 1/06
                                                              248/478
4,109,821 A *  8/1978 Lutz .............................. 220/836
(Continued)

FOREIGN PATENT DOCUMENTS

CN         1411874 A      4/2003
CN         1520893 A      8/2004
(Continued)

OTHER PUBLICATIONS

International Search Report completed Jun. 28, 2012 dated Jun. 29, 2012 from corresponding International Application No. PCT/US2011/061825 filed Nov. 22, 2011 (3 pages).
(Continued)

*Primary Examiner* — Nathan R Price
*Assistant Examiner* — Justin L Zamory
(74) *Attorney, Agent, or Firm* — Klein, O'Neill & Singh, LLP

(57) ABSTRACT

Embodiments of the shield assemblies include a shield that is pivotably secured to a needle hub. A ball-and-socket hinge secures the shield and the hub to one another. The assembly includes a reversible shield lock to hold the shield in the needle-protected position.

27 Claims, 12 Drawing Sheets

FIG. 5

(58) Field of Classification Search
CPC .... A61M 5/3293; A61M 5/344; A61M 5/345; A61M 5/347; A61M 2005/3206; F16C 11/0614; Y10T 16/524; Y10T 16/544
USPC .......... 604/110, 192, 263; 128/919; 403/56
See application file for complete search history.

(56) References Cited

U.S. PATENT DOCUMENTS

| | | |
|---|---|---|
| 4,620,813 A * | 11/1986 | Lacher ................. F16C 11/106 248/182.1 |
| 4,658,471 A * | 4/1987 | Nakanishi ............. B21D 53/40 16/224 |
| 4,886,503 A | 12/1989 | Miller |
| 4,982,842 A | 1/1991 | Hollister |
| 5,011,475 A | 4/1991 | Olson |
| 5,139,489 A | 8/1992 | Hollister |
| 5,154,285 A | 10/1992 | Hollister |
| 5,232,454 A | 8/1993 | Hollister |
| 5,232,455 A | 8/1993 | Hollister |
| 5,277,311 A | 1/1994 | Hollister |
| 5,312,368 A | 5/1994 | Haynes |
| 5,370,628 A | 12/1994 | Allison et al. |
| 5,385,551 A | 1/1995 | Shaw |
| 5,389,076 A | 2/1995 | Shaw |
| 5,419,766 A | 5/1995 | Chang et al. |
| 5,423,758 A | 6/1995 | Shaw |
| 5,423,765 A | 6/1995 | Hollister |
| 5,423,766 A | 6/1995 | Di Cesare |
| 5,433,711 A | 7/1995 | Balaban et al. |
| 5,447,501 A | 9/1995 | Karlsson et al. |
| 5,466,223 A | 11/1995 | Bressler et al. |
| 5,486,163 A | 1/1996 | Haynes |
| 5,487,733 A | 1/1996 | Caizza et al. |
| 5,490,841 A | 2/1996 | Landis |
| 5,509,907 A | 4/1996 | Bevilacqua |
| 5,533,974 A | 7/1996 | Gaba |
| 5,536,257 A | 7/1996 | Byrne et al. |
| 5,584,816 A | 12/1996 | Gyure et al. |
| 5,588,767 A * | 12/1996 | Merlo ................. F16C 11/106 403/103 |
| 5,599,313 A | 2/1997 | Gyure et al. |
| 5,599,318 A * | 2/1997 | Sweeney ............. A61M 5/3216 128/919 |
| 5,603,699 A | 2/1997 | Shine |
| 5,615,771 A | 4/1997 | Hollister |
| 5,632,732 A | 5/1997 | Szabo et al. |
| 5,643,219 A | 7/1997 | Burns |
| 5,649,622 A | 7/1997 | Hollister |
| 5,662,617 A | 9/1997 | Odell et al. |
| 5,669,889 A | 9/1997 | Gyure et al. |
| 5,681,295 A | 10/1997 | Gyure et al. |
| 5,693,022 A | 12/1997 | Haynes |
| 5,704,920 A | 1/1998 | Gyure |
| 5,733,265 A | 3/1998 | Bachman et al. |
| 5,743,888 A | 4/1998 | Wilkes et al. |
| 5,746,726 A * | 5/1998 | Sweeney ............. A61M 5/3216 604/192 |
| 5,807,351 A | 9/1998 | Kashmer |
| 5,810,775 A | 9/1998 | Shaw |
| 5,823,997 A | 10/1998 | Thorne |
| 5,836,920 A | 11/1998 | Robertson |
| 5,868,716 A | 2/1999 | Sweeney et al. |
| 5,885,249 A | 3/1999 | Irisawa |
| 5,891,103 A | 4/1999 | Burns |
| 5,913,846 A | 6/1999 | Szabo |
| 5,919,165 A | 7/1999 | Benson |
| 5,957,892 A | 9/1999 | Thorne |
| 5,980,488 A | 11/1999 | Thorne |
| RE36,447 E | 12/1999 | Byrne et al. |
| 6,042,570 A | 3/2000 | Bell et al. |
| 6,096,024 A | 8/2000 | Graves et al. |
| 6,120,480 A | 9/2000 | Zhang et al. |
| 6,149,629 A | 11/2000 | Wilson et al. |
| RE37,110 E | 3/2001 | Hollister |
| RE37,252 E | 7/2001 | Hollister |
| 6,254,575 B1 | 7/2001 | Thorne, Jr. et al. |
| 6,280,420 B1 | 8/2001 | Ferguson et al. |
| 6,298,541 B1 | 10/2001 | Newby et al. |
| 6,319,232 B1 | 11/2001 | Kashmer |
| 6,328,713 B1 | 12/2001 | Hollister |
| 6,334,857 B1 | 1/2002 | Hollister et al. |
| 6,355,021 B1 | 3/2002 | Nielsen et al. |
| 6,436,086 B1 | 8/2002 | Newby et al. |
| 6,440,104 B1 | 8/2002 | Newby et al. |
| 6,517,522 B1 | 2/2003 | Bell et al. |
| 6,524,281 B1 | 2/2003 | Hudon |
| 6,551,287 B2 | 4/2003 | Hollister et al. |
| 6,561,476 B2 * | 5/2003 | Carnevali ............. F16M 11/14 248/181.1 |
| 6,582,397 B2 | 6/2003 | Alesi et al. |
| 6,592,556 B1 | 7/2003 | Thorne |
| 6,616,638 B2 | 9/2003 | Peters, III |
| 6,635,032 B2 | 10/2003 | Ward, Jr. |
| 6,648,855 B2 | 11/2003 | Crawford et al. |
| 6,699,217 B2 | 3/2004 | Bennett et al. |
| 6,719,737 B2 | 4/2004 | Kobayashi |
| 6,752,788 B2 | 6/2004 | Tuen |
| 6,780,169 B2 | 8/2004 | Crawford |
| 6,811,547 B2 | 11/2004 | Wilkinson |
| 6,824,531 B1 | 11/2004 | Zecha, Jr. et al. |
| 6,840,922 B2 | 1/2005 | Nielsen et al. |
| 6,869,418 B2 | 3/2005 | Marano-Ford |
| D505,200 S | 5/2005 | Simpson et al. |
| 6,918,891 B2 | 7/2005 | Bressler et al. |
| 6,921,388 B2 | 7/2005 | Swenson |
| 6,951,551 B2 | 10/2005 | Hudon |
| 7,001,363 B2 | 2/2006 | Ferguson et al. |
| RE39,107 E | 5/2006 | Shaw |
| 7,112,190 B2 | 9/2006 | Bressler et al. |
| 7,128,726 B2 | 10/2006 | Crawford et al. |
| 7,147,623 B2 | 12/2006 | Mathiasen |
| 7,163,526 B2 | 1/2007 | Leong et al. |
| 7,186,240 B1 | 3/2007 | Kronja |
| 7,198,618 B2 | 4/2007 | Ferguson et al. |
| 7,201,736 B2 | 4/2007 | Hauri |
| 7,220,249 B2 | 5/2007 | Hwang et al. |
| 7,223,258 B2 | 5/2007 | Crawford |
| 7,250,038 B2 | 7/2007 | Simpson et al. |
| 7,316,668 B2 | 1/2008 | Swenson |
| 7,322,963 B2 | 1/2008 | Goh |
| 7,361,159 B2 | 4/2008 | Fiser et al. |
| 7,387,615 B2 | 6/2008 | Coelho et al. |
| 7,413,560 B2 | 8/2008 | Chong et al. |
| 7,488,306 B2 | 2/2009 | Nguyen |
| 7,537,581 B2 | 5/2009 | Hwang |
| 7,553,296 B2 | 6/2009 | Bedford et al. |
| 7,591,800 B2 | 9/2009 | Nguyen |
| 7,632,252 B2 | 12/2009 | Prais et al. |
| 7,635,352 B2 | 12/2009 | Adams |
| 7,648,480 B2 | 1/2010 | Bosel et al. |
| 7,717,877 B2 | 5/2010 | Lavi et al. |
| 7,722,572 B2 | 5/2010 | Sprinkle et al. |
| 7,803,138 B2 | 9/2010 | Bressler et al. |
| 7,811,261 B2 | 10/2010 | Rubinstein et al. |
| 7,833,198 B2 | 11/2010 | Bressler et al. |
| 7,854,723 B2 | 12/2010 | Hwang et al. |
| 7,862,547 B2 | 1/2011 | Ferguson et al. |
| 7,871,397 B2 | 1/2011 | Schraga |
| 7,938,800 B2 | 5/2011 | Koh |
| 7,951,090 B2 | 5/2011 | Sarstedt |
| 7,967,794 B2 | 6/2011 | Bosel et al. |
| 8,016,796 B2 | 9/2011 | Simas, Jr. et al. |
| 8,029,463 B2 | 10/2011 | Hauri |
| 8,038,654 B2 | 10/2011 | Lim et al. |
| 8,057,431 B2 | 11/2011 | Woehr et al. |
| 8,061,007 B2 | 11/2011 | Simpson et al. |
| 8,100,858 B2 | 1/2012 | Woehr et al. |
| 8,109,910 B2 | 2/2012 | Zastawny et al. |
| 8,152,761 B2 | 4/2012 | Hauri et al. |
| 8,162,882 B2 | 4/2012 | Rubinstein et al. |
| 8,167,851 B2 | 5/2012 | Sen |
| 8,172,809 B2 | 5/2012 | Ferguson et al. |
| 8,177,063 B1 | 5/2012 | Simm et al. |

(56) References Cited

U.S. PATENT DOCUMENTS

| | | | |
|---|---|---|---|
| 8,182,451 B2 | 5/2012 | Bressler et al. | |
| 8,226,576 B2 | 7/2012 | Swenson et al. | |
| 8,226,604 B2 | 7/2012 | Madin et al. | |
| 8,226,617 B2 | 7/2012 | Ferguson et al. | |
| 8,231,583 B2 | 7/2012 | Swenson | |
| 8,251,961 B2 | 8/2012 | Hauri et al. | |
| 8,277,408 B2 | 10/2012 | Crawfprd et al. | |
| 8,287,498 B2 | 10/2012 | Tan et al. | |
| 8,425,472 B2 | 4/2013 | Bressler et al. | |
| 8,608,695 B2 | 12/2013 | Hauri et al. | |
| 8,622,960 B2 | 1/2014 | Madin et al. | |
| 8,641,680 B2 | 2/2014 | Simas, Jr. | |
| 8,708,977 B2 | 4/2014 | Bressler et al. | |
| 8,827,955 B2 | 9/2014 | Haindl et al. | |
| 2002/0062107 A1 | 5/2002 | Parmigiani et al. | |
| 2002/0072715 A1* | 6/2002 | Newby | A61B 5/150587 604/192 |
| 2003/0060773 A1 | 3/2003 | Nguyen | |
| 2003/0078548 A1 | 4/2003 | Kobayashi | |
| 2003/0125676 A1 | 7/2003 | Swenson et al. | |
| 2003/0181860 A1 | 9/2003 | Swenson | |
| 2003/0181868 A1 | 9/2003 | Swenson | |
| 2003/0187398 A1 | 10/2003 | Crawford | |
| 2003/0187399 A1 | 10/2003 | Crawford | |
| 2003/0191438 A1 | 10/2003 | Ferguson et al. | |
| 2003/0220618 A1 | 11/2003 | Crawford | |
| 2004/0044318 A1 | 3/2004 | Fiser et al. | |
| 2004/0054334 A1 | 3/2004 | Prais et al. | |
| 2004/0059302 A1 | 3/2004 | Crawford et al. | |
| 2004/0078007 A1 | 4/2004 | Nguyen | |
| 2005/0004531 A1 | 1/2005 | Hwang et al. | |
| 2005/0065481 A1 | 3/2005 | Hauri et al. | |
| 2005/0124944 A1 | 6/2005 | Hwang | |
| 2005/0146081 A1 | 7/2005 | MacLean et al. | |
| 2006/0052748 A1 | 3/2006 | Coelho et al. | |
| 2006/0149188 A1 | 7/2006 | Simas, Jr. | |
| 2006/0200078 A1 | 9/2006 | Konrad | |
| 2006/0224122 A1 | 10/2006 | Bosel et al. | |
| 2006/0270947 A1 | 11/2006 | Crawford et al. | |
| 2006/0270979 A1 | 11/2006 | Simas, Jr. et al. | |
| 2007/0088261 A1 | 4/2007 | Lew et al. | |
| 2007/0156088 A1 | 7/2007 | Hauri | |
| 2007/0274770 A1* | 11/2007 | Sagisaka | F16C 11/0638 403/132 |
| 2008/0208138 A1 | 8/2008 | Lim et al. | |
| 2008/0306451 A1* | 12/2008 | Woehr | A61M 5/3216 604/198 |
| 2009/0173330 A1* | 7/2009 | Akins | F41B 11/52 124/45 |
| 2011/0288496 A1 | 11/2011 | Harms et al. | |
| 2011/0301546 A1 | 12/2011 | Harms et al. | |
| 2013/0237927 A1 | 9/2013 | Sim et al. | |
| 2013/0274684 A1 | 10/2013 | Bubenik et al. | |
| 2013/0331793 A1 | 12/2013 | Gonzales et al. | |
| 2014/0052072 A1 | 2/2014 | Simas, Jr. et al. | |
| 2014/0135713 A1 | 5/2014 | Domonkos | |

FOREIGN PATENT DOCUMENTS

| | | |
|---|---|---|
| CN | 2763429 Y | 3/2006 |
| CN | 103269740 A | 8/2013 |
| DE | 69722333 T2 | 3/2004 |
| EP | 0433250 A2 | 6/1991 |
| EP | 0887082 A2 | 12/1998 |
| EP | 1380315 A1 | 1/2004 |
| FR | 2640674 A | 6/1990 |
| JP | 11-124158 A | 5/1999 |
| JP | H11-299692 A | 11/1999 |
| JP | 2002 102344 A | 4/2002 |
| JP | 2004-525741 A | 8/2004 |
| JP | 2005-521537 A | 7/2005 |
| JP | 2006-183709 A | 7/2006 |
| JP | 2009-513301 A | 4/2009 |
| JP | 2013-545548 A | 12/2013 |
| JP | 2014-520590 A | 8/2014 |
| WO | WO 2006/041442 | 4/2006 |
| WO | WO 2008/076459 A1 | 6/2008 |
| WO | WO 2010/059345 A2 | 5/2010 |
| WO | WO 2012/071400 A2 | 5/2012 |
| WO | WO 2012/111560 A1 | 8/2012 |
| WO | WO 2012/152207 A1 | 11/2012 |
| WO | WO 2013006134 | 1/2013 |
| WO | WO 2013134498 | 9/2013 |

OTHER PUBLICATIONS

Written Opinion completed Jun. 28, 2012 dated Jun. 29, 2012 from corresponding International Application No. PCT/US2011/061825 filed Nov. 22, 2011 (4 pages).
Examiner's Report on corresponding foreign application (RU Application No. 2013128474) from the Patent Office of the Russian Federation dated Apr. 30, 2015.
Examiner's Report on corresponding foreign application (CN Application No. 201180056060.X) from the State Intellectual Property Office dated Sep. 29, 2014.
Examiner's Report on corresponding foreign application (JP Application No. 2013-541017) from the Japanese Intellectual Property Office dated Oct. 20, 2015.
Examiner's Report on corresponding foreign application (CN Application No. 201180056060.X) from the State Intellectual Property Office dated Jan. 4, 2016.
Decision on Grant on corresponding foreign application (RU Application No. 2013128474) from the Russian Patent Office dated Jan. 13, 2016.
Non-Final Office Action on related U.S. Appl. No. 14/662,678 dated Apr. 6, 2017.
Notice of Allowance on related U.S. Appl. No. 14/662,678 dated Mar. 21, 2018.
Examination Report on corresponding foreign application (EP Application No. 16712002.1) from the European Patent Office dated Aug. 3, 2018.
International Search Report and Written Opinion on corresponding PCT application (PCT/EP2016/055715) from International Searching Authority (EPO) dated May 17, 2016.
International Preliminary Report on Patentability on corresponding PCT application (PCT/EP2016/055715) from International Searching Authority (EPO) dated Sep. 28, 2017.
Final Office Action on related U.S. Appl. No. 14/662,678 dated Oct. 19, 2017.
Decision of Reexamination on corresponding foreign application (CN Application No. 201180056060.X) from the State Intellectual Property Office dated Nov. 24, 2017.
Office Action on corresponding foreign application (DE Application No. 11 2011 103 856.9) from the German Patent Office dated Feb. 20, 2018.
Office Action on corresponding foreign application (AU Application No. 2016232180) from the Australian Patent Office dated Oct. 14, 2019.
Office Action on corresponding foreign application (EP Application No. 16712002.1) from the Australian Patent Office dated Oct. 30, 2019.
English translation of an Office Action including search report on corresponding foreign application (BR Application No. BR112013012582-9) from the Brazilian Patent Office dated Aug. 1, 2019.
Office Action on corresponding foreign application (CN Application No. 201180056060.X) from the State Intellectual Property Office, P.R. China dated Jun. 19, 2015.
Decision on Rejection on corresponding foreign application (CN Application No. 201180056060.X) from the State Intellectual Property Office, P.R. China dated Jul. 25, 2016.
Office Action on corresponding foreign application (IN Application No. 1271/DELNP/2013) from the Indian Intellectual Property Office dated Aug. 30, 2019.
Decision to Grant on corresponding foreign application (JP Application No. 2013541017) from the Japan Patent Office dated Apr. 11, 2017.

(56) References Cited

OTHER PUBLICATIONS

Office Action on corresponding foreign application (JP Application No. 2017-540613) from the Japan Patent Office dated Jan. 21, 2020.
International Preliminary Report on Patentability (Chapter I) on corresponding PCT application (PCT/US2011/061825) from International Searching Authority (KR) dated May 30, 2013.
Office Action on corresponding foreign application (CN Application No. 201680016777.4) from the National Intellectual Property Administration, P.R. China dated Dec. 11, 2019.

* cited by examiner

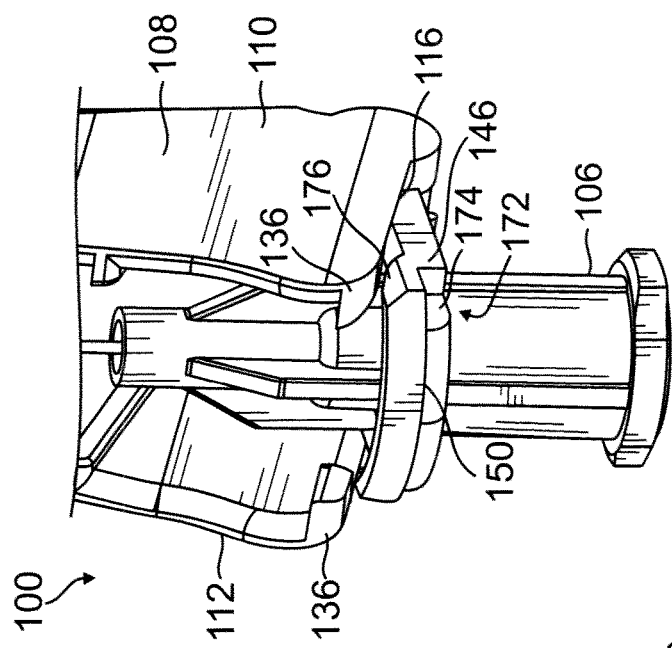
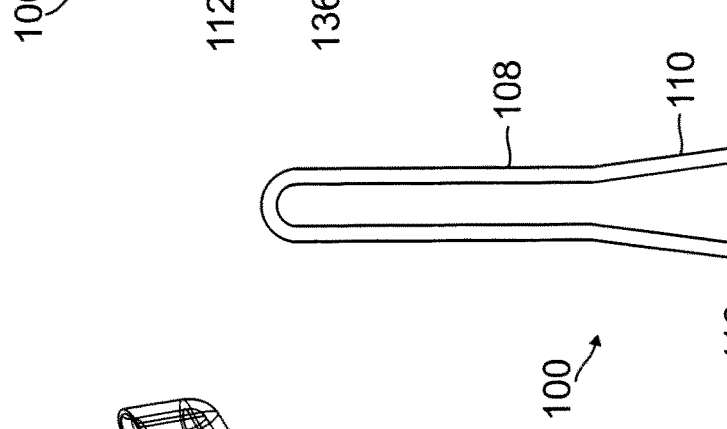
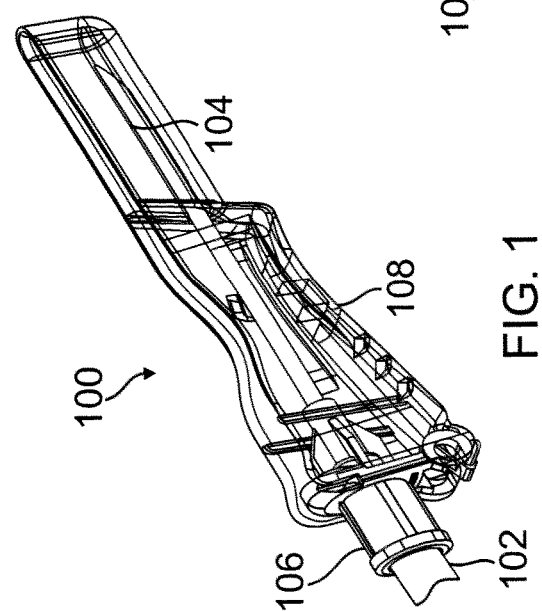

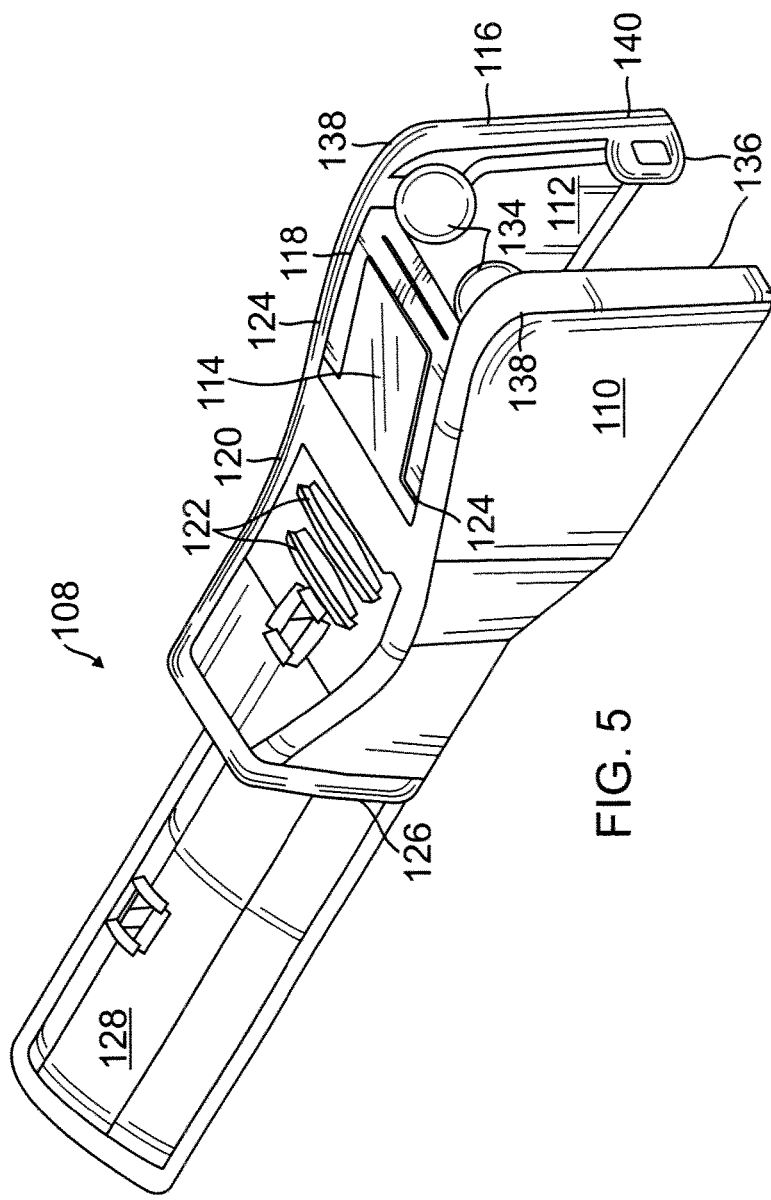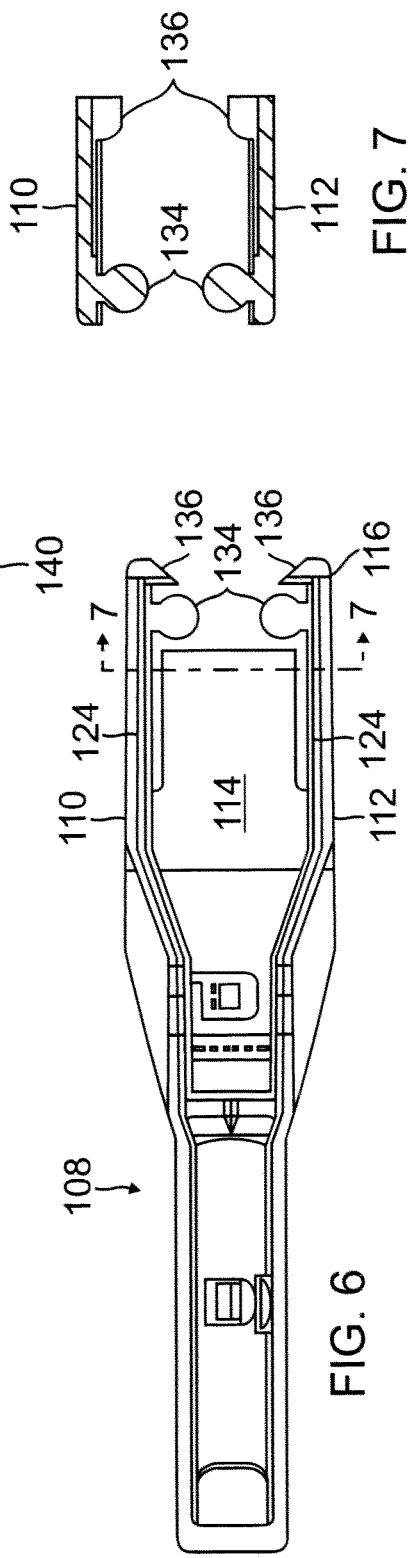

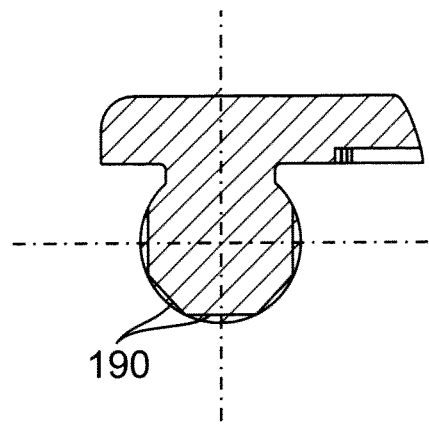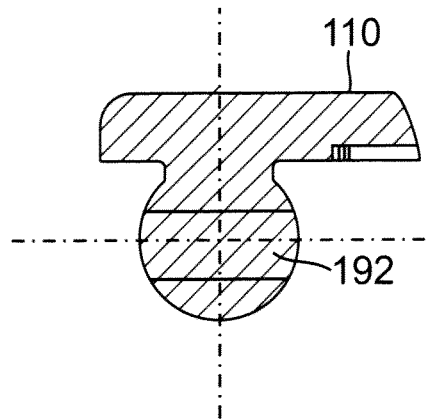
FIG. 8    FIG. 9
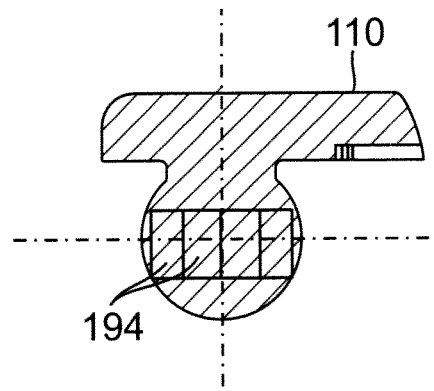
FIG. 10
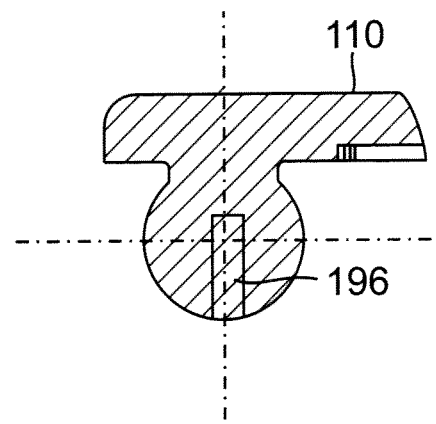
FIG. 11

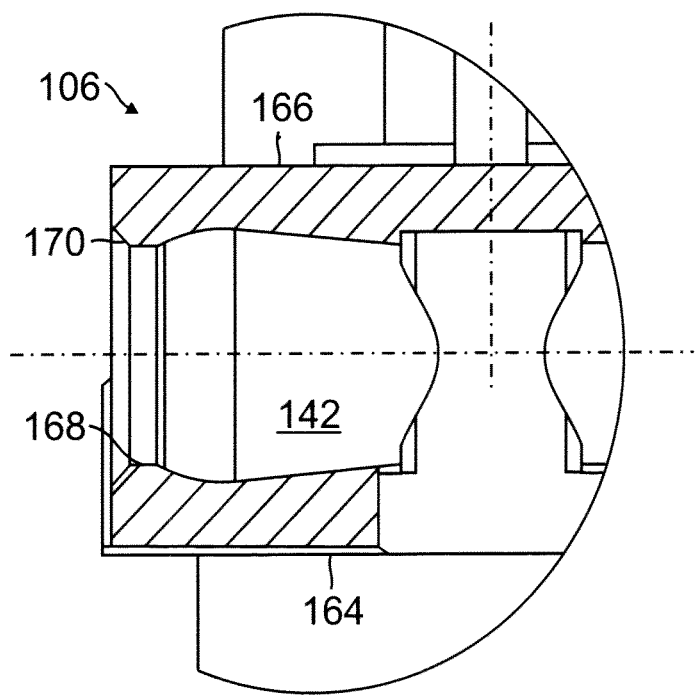
FIG. 15
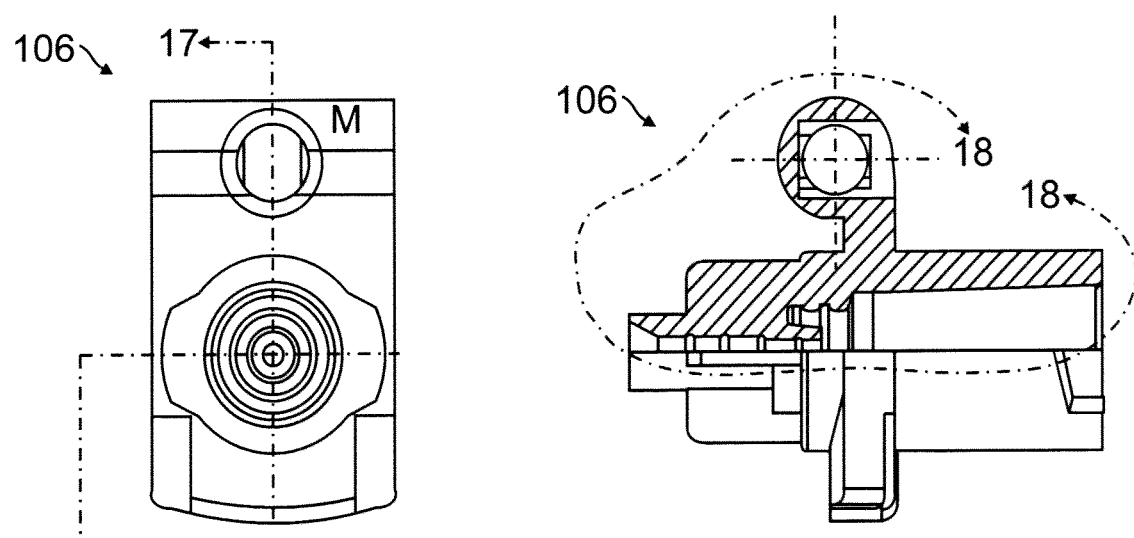
FIG. 16
FIG. 17

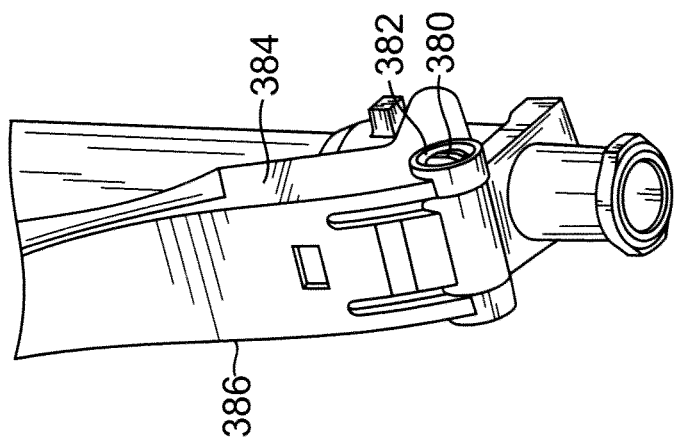
FIG. 37
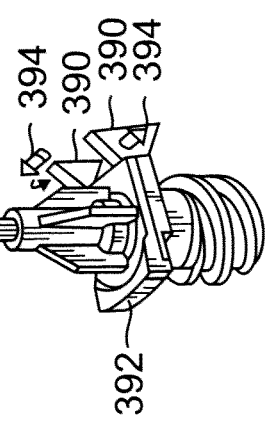
FIG. 36
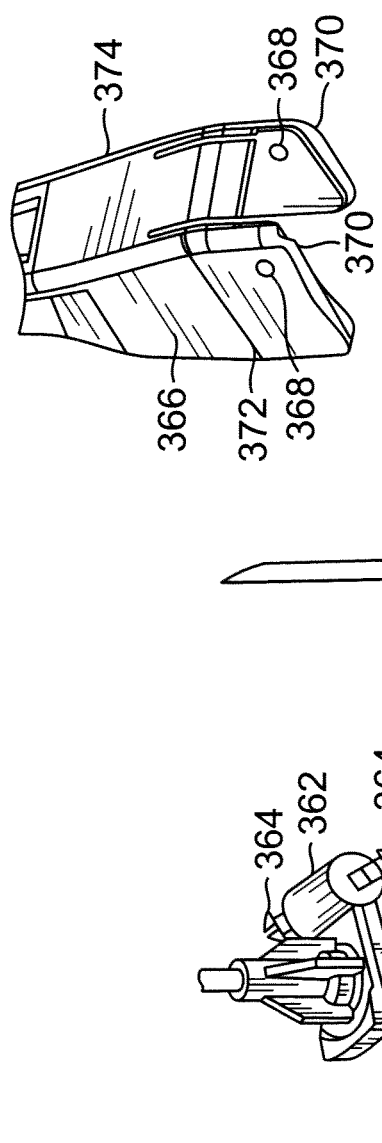
FIG. 35
FIG. 34

HINGED SHIELD ASSEMBLIES AND RELATED METHODS

TECHNICAL FIELD

Shields for needle devices are generally discussed herein with hinged shield devices for use with hypodermic needles more particularly discussed.

BACKGROUND

Recapping is a common procedure for periods between drawing up fluids into a syringe and administering injections through a needle. The recapping procedure can occasionally cause needlesticks since users sometime misalign the needles with the openings on the caps. Injuries can also occur after an injection and prior to the discarding of the needles. Needlesticks can be painful, but can also cause great inconvenience because all needlesticks must be reported. Also, since needles related to needlesticks must be discarded, medications contained within the syringes are unnecessarily wasted. Furthermore, fluids linked to these "clean" type of needlesticks can cause injuries and adverse reactions.

SUMMARY

The various embodiments of the present hinged shield assemblies and related methods have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide advantages, which include the capability to hold the shield in any desired orientation with respect to the needle hub without having to manually grasp or handle the shield.

One aspect of the present hinged shield assemblies includes the realization that many contemporary hinged shield assemblies use a "living" hinge. A living hinge is a relatively thin portion of injection-molded plastic that joins the first and second hinged components in a unitary construction. With respect to hinged shield assemblies for covering needles, living hinges have at least one drawback: they do not remain at the position which they are opened and even tend to bias toward the needle-protected position. Thus, when the needle and shield assembly are used to perform an injection or blood draw, the operator may need to use his or her finger(s) to manually hold the shield away from the needle. In certain instances, a retention mechanism is used to hold or keep the cap at a temporary fixed position. The living hinge thus makes the procedure more cumbersome unless means is provided to compensate for the noted issues.

One embodiment of the present hinged shield assemblies comprises a needle hub including a first hinge part. A needle extends from the needle hub. The shield assembly further comprises a shield including a second hinge part that engages the first hinge part to pivotably secure the shield to the hub. The shield further includes a plurality of side walls configured to partially surround the needle when the shield assembly is in a protected position. One of the first and second hinge parts defines a first ball and a second ball and the other of the first and second hinge parts defines a first socket and a second socket. The first and second sockets receive the first and second balls in pivotable engagement.

One embodiment of the present methods comprises a method of making a hinged shield assembly configured to shield a needle to prevent needlesticks. The assembly includes a needle hub and a shield. The shield further includes a plurality of side walls configured to partially surround the needle when the shield assembly is in a protected position. The method comprises forming the needle hub with a first hinge part and securing the needle to the needle hub. The method further comprises forming the shield with a second hinge part. The method further comprises engaging the first hinge part and the second hinge part with one another to pivotably secure the shield to the hub. One of the first and second hinge parts defines a first ball and a second ball and the other of the first and second hinge parts defines a first socket and a second socket. The first and second sockets receive the first and second balls in pivotable engagement.

Another embodiment of the present methods comprises a method of using a hinged shield assembly to shield a needle to prevent needlesticks. The assembly includes a needle hub and a shield. The shield further includes a plurality of side walls. The method comprises pivoting the shield with respect to the hub about a hinge that pivotably secures the shield to the hub. The method further comprises continuing to pivot the shield with respect to the hub until the side walls partially surround the needle in a protected position. The method further comprises locking the shield with respect to the hub or with respect to the needle in the protected position. Pivoting the shield with respect to the hub about the hinge comprises pivoting a first ball within a first socket and pivoting a second ball within a second socket.

BRIEF DESCRIPTION OF THE DRAWINGS

The various embodiments of the present hinged shield assemblies now will be discussed in detail with an emphasis on highlighting the advantageous features. These embodiments depict the novel and non-obvious hinged shield assemblies shown in the accompanying drawings, which are for illustrative purposes only. These drawings include the following figures, in which like numerals indicate like parts:

FIG. 1 is a side perspective view of one embodiment of the present hinged shield assemblies in a protected position;

FIG. 2 is a front elevation view of the needle hub and the shield of the hinged shield assembly of FIG. 1, showing the hub and shield rotated 90° with respect to one another about the hinge from the configuration of FIG. 1;

FIG. 3 is a lower perspective view of the hinged shield assembly of FIG. 1, showing a reversible shield lock of the assembly in an unlocked position;

FIG. 5 is a lower/side perspective view of the shield of the hinged shield assembly of FIG. 1;

FIG. 6 is a front elevation view of the shield of FIG. 5;

FIG. 7 is a cross-sectional view of the shield of FIG. 6 taken through the line 7-7 in FIG. 6;

FIG. 8 is a cross-sectional detail view of one alternative shape of the ball portion of the shield of FIGS. 5-7;

FIG. 9 is a cross-sectional detail view of another alternative shape of the ball portion of the shield of FIGS. 5-7;

FIG. 10 is a cross-sectional detail view of another alternative shape of the ball portion of the shield of FIGS. 5-7;

FIG. 11 is a cross-sectional detail view of another alternative shape of the ball portion of the shield of FIGS. 5-7;

FIG. 15 is a detail view of the portion of FIG. 14 indicated by the circle 15-15;

FIG. 16 is a lower elevation view of the hub of FIG. 12;

FIG. 17 is a partial cross-sectional view of the hub of FIG. 16 taken through the line 17-17 in FIG. 16;

FIG. 34 is a side perspective view of an alternative configuration of a needle hub of the present hinged shield assemblies;

FIG. 35 is a side perspective view of an alternative configuration of a needle hub of the present hinged shield assemblies;

FIG. 36 is a lower/rear perspective view of an alternative configuration of a shield of the present hinged shield assemblies, the shield being compatible with the hubs of FIGS. 34 and 35;

FIG. 37 is a lower/rear perspective view of an assembly including a needle hub similar to that of FIG. 34 and a shield similar to that of FIG. 36;

DETAILED DESCRIPTION

Figure 4:
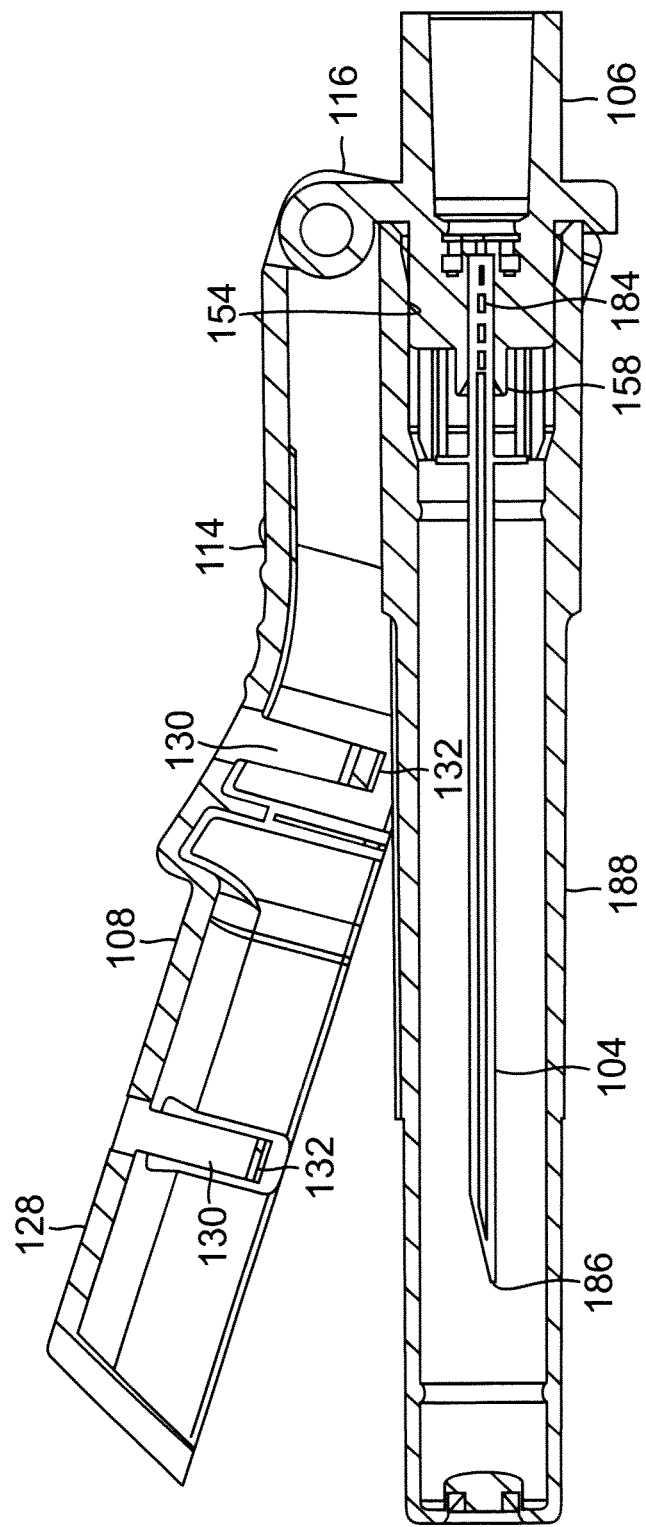
FIG. 4 is a side cross-sectional view of the hinged shield assembly of FIG. 1, in a shipping configuration and including a removable needle cap.

The following detailed description describes the present embodiments, including apparatuses, devices, and methods, with reference to the drawings. In the drawings, reference numbers label elements of the present embodiments. These reference numbers are reproduced below in connection with the discussion of the corresponding drawing features.

FIGS. 1-18 illustrate different variations of hinged shield assemblies and their components. The hinged shield assembly 100 cooperates with a syringe 102 (FIG. 1, partially shown) and comprises a shield 108 to selectively shield a needle 104 (FIGS. 1 and 4) extending from a needle hub 106, which engages a distal end of the syringe 102. With reference to FIGS. 1 and 3, the shield assembly 100 comprises the hub 106 and the shield 108 that is pivotable about the hub 106. As described in further detail below, the shield 108 is configured to be manipulated from a packaged position (FIG. 4) to a ready-to-use position (FIG. 3), from the ready-to-use position to an open position (FIG. 2), and from the open position to a secured position (FIG. 1).

With reference to FIGS. 5-7, the shield 108 comprises first, second and third sidewalls 110, 112, 114 configured to surround the needle 104 on three sides. The third sidewall 114 may also be referred to as a center wall or rear wall and is positioned between the first and second sidewalls 110, 112. With reference to FIG. 6, the first and second sidewalls 110, 112 are generally parallel to one another at a base end 116 of the shield 108, then taper toward one another, and then continue parallel to one another. With reference to FIG. 5, the third sidewall 114 is contoured from a sloping base portion 118 to a concave portion 120. An outside surface of the concave portion 120 includes transverse ridges 122 that facilitate gripping the shield 108. All three sidewalls 110, 112, 114 are joined at approximately 90° angles. However, near the base 116 of the shield 108 the first and second sidewalls 110, 112 are slightly spaced from the third sidewall 114, forming first and second slits 124 (FIG. 6). The slits 124 enable the first and second sidewalls 110, 112 to be bent away from one another to facilitate mounting the shield 108 on the hub 106 during manufacture, as further described below.

With reference to FIG. 5, the sidewalls 110, 112, 114 extend approximately half the length of the shield 108 and adjoin a shoulder portion 126 that extends transversely inward from the edges of all three sidewalls 110, 112, 114. A shroud 128 extends from the shoulder portion 126 away from the sidewalls 110, 112, 114. The shroud 128 has a substantially U-shaped cross-section. The shroud 128 is closed at its end opposite the base end 116 of the shield 108. The shield 108 is open along one side to accommodate passage of the needle 104 as the shield 108 pivots with respect to the hub 106, as explained in detail below.

With reference to FIGS. 4 and 6, the shield 108 further comprises first and second hooks 130 that extend inwardly from the third sidewall 114 and from the shroud 128. In the illustrated embodiment, the hooks 130 are formed integrally with the shield 108. The hooks 130 are configured to capture the needle 104 when the shield 108 is pivoted toward the needle 104 to secure the shield 108 in the needle-protected position. As the shield 108 pivots toward the needle 104, a ramped or rounded end surface 132 of each hook 130 contacts the needle 104, flexing the hook 130 laterally to allow the hook 130 to snap around and capture the needle 104. In other examples, one hook or more than two hooks may be incorporated. In still other examples, the location of the hooks may be changed so that the hooks secure different sections of the needle and/or the needle hub.

With reference to FIGS. 5-7, the base end 116 of the shield 108 includes first and second ball joints or balls 134 and first and second tabs 136. The balls 134 extend inwardly from inner surfaces of the first and second sidewalls 110, 112 adjacent first corners 138 thereof. The tabs 136 extend inwardly from the inner surfaces of the first and second sidewalls 110, 112 adjacent second corners 140 thereof. With reference to FIG. 2, the balls 134 are configured to be received within sockets 142 on the hub 106 to form a ball-and-socket hinge 144 for pivotal movement of the shield 108 and hub 106 with respect to one another. Thus, the hinge 144 is understood to include two or more separately formed components, i.e., a multi-piece, that are joined together to form a movable hinge. With reference to FIG. 3, the tabs 136 are configured to be received beneath ledges 146 on the hub 106 to secure the shield 108 in the needle-protected position. These aspects are described in detail below.

Figure 13:
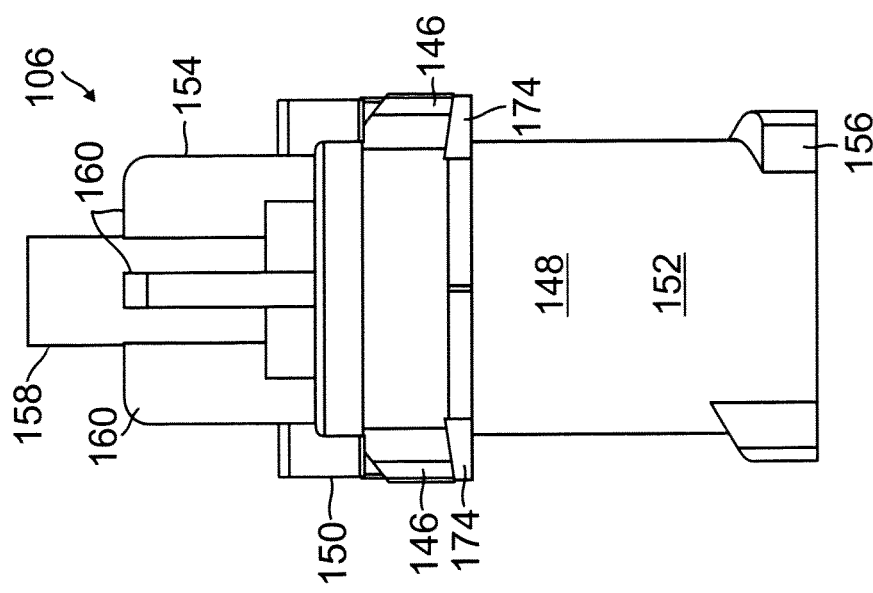
FIG. 13 is a rear elevation view of the hub of FIG. 12.
Figure 12:
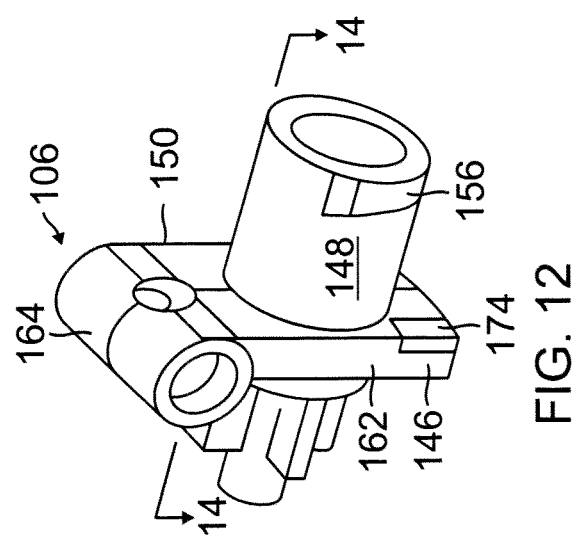
FIG. 12 is a lower/side perspective view of the needle hub of the hinged shield assembly of FIG. 1.

FIGS. 12-18 illustrate the hub 106 in detail. With reference to FIGS. 12 and 13, the hub 106 includes a cylindrical portion 148 and a transverse base portion 150. The base portion 150 substantially bisects the cylindrical portion 148, defining a proximal cylindrical portion 152 and a distal cylindrical portion 154 (FIG. 13). The proximal cylindrical portion 152 is shaped as a smooth hollow cylinder and includes a male thread 156 at its proximal end. The male thread 156 is configured to engage a female thread at a distal end of a syringe (not shown) to secure the shield 108 to the syringe. The distal cylindrical portion 154 includes a hollow cylinder 158 having fins 160 extending outwardly and parallel to an axis of the cylinder 158. Four evenly spaced fins 160 are shown, but any number may be provided. The hollow cylinder 158 is configured to receive the blunt proximal end of a needle 104 in a glued engagement with the needle 104 disposed inside the cylinder 158, as shown in FIG. 4. In an alternative embodiment, the engagement can be a press-fit engagement.

Figure 14:
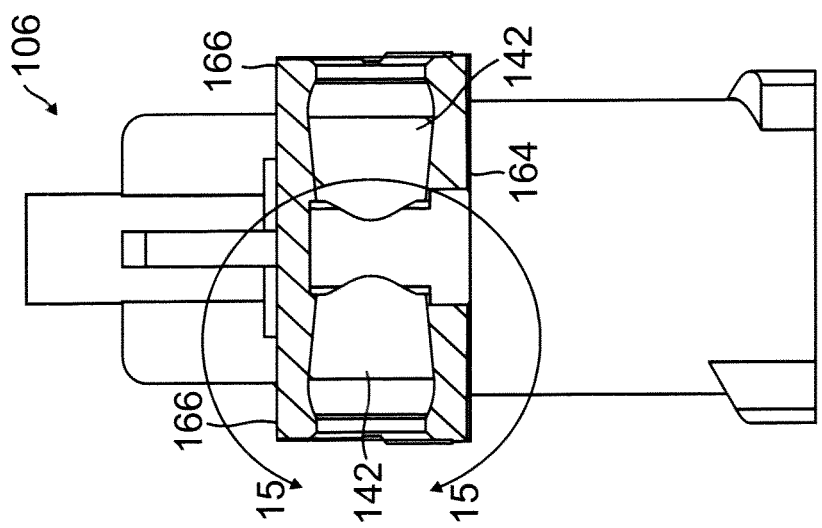
FIG. 14 is a partial cross-sectional view of the hub of FIG. 13 taken through the line 14-14 in FIG. 13.

With reference to FIGS. 3, 12 and 13, the transverse base portion 150 includes a substantially planar portion 162 that adjoins at one end a hinge component 164, which in the present embodiment is a substantially cylindrical portion 164. As shown in FIGS. 14 and 15, the cylindrical portion 164 comprises first and second socket parts 166 of the ball-and-socket hinge 144. With reference to FIG. 15, each socket part 166 includes an opening 168 having a beveled rim 170. From the opening 168, the diameter of the socket part 166 varies from the relatively narrow opening 168, with the diameter abruptly increasing inward of the opening 168 and then gently tapering down to a more narrow diameter. This variable diameter opening is configured to receive a ball of the ball and socket hinge.

The changes in diameter in the socket parts 166 create the sockets 142 that receive the balls 134, as shown in FIG. 2. Each ball 134 has a diameter that is approximately equal to the maximum diameter of each socket 142, but greater than the diameter of the opening 168 (FIG. 15). The balls 134 thus sit within the sockets 142 and resist withdrawal from the sockets 142 because the opening 168 has a smaller diameter than the diameter of each ball 134. The relative sizes of the balls 134 and sockets 142 can be tailored to provide a desired amount of resistance to rotation of the balls 134 within the sockets 142 and degree of interference. Also, the shapes of the balls 134 can be tailored to provide a desired smoothness of motion, or lack of smoothness, as described below.

With reference to FIGS. 3, 12 and 13, the needle hub 106 further comprises a first part 146 of a reversible shield lock 172. At the corners opposite the sockets 142, the hub 106 includes ledges 146 that form notches 174 on the proximal side of the transverse base 150. The notches 174 are sized and shaped to be complementary to the tabs 136 on the shield 108. The tabs 136 snap into the notches 174 when the shield 108 is pivoted toward the needle-protected position to hold the shield 108 in that position. With reference to FIG. 3, the surfaces 176 of the ledges 146 opposite the notches 174 are ramped so that as the shield 108 pivots toward the protected position the tabs 136 slide over the ramps 176 and deflect outwardly. When the tabs 136 slide around the ledges 146, they snap into the notches 174 to resist pivoting of the shield 108 away from the protected position. However, the locking action provided by the tabs 136, notches 174 and ledges 146 is reversible. An operator may apply digital pressure to flex the first and second sidewalls 110, 112 away from one another. By flexing the sidewalls sufficiently, the tabs 136 can clear the ledges 146 so that the shield 108 can be pivoted away from the protected position.

Figure 18:
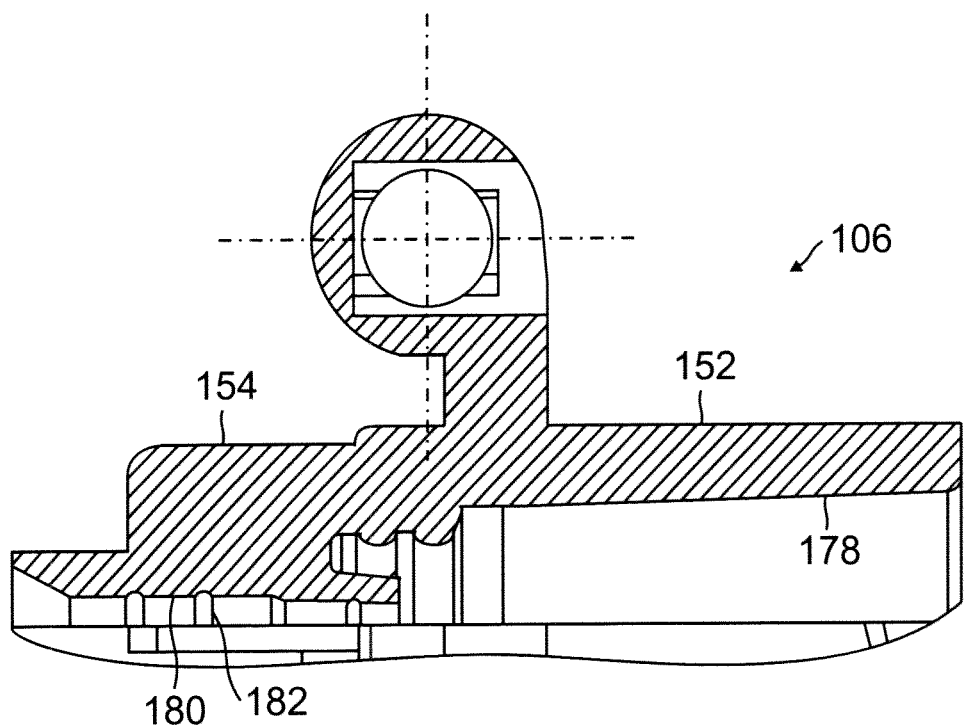
FIG. 18 is a detail view of the portion of FIG. 17 indicated by the shape 18-18.
Figure 19:
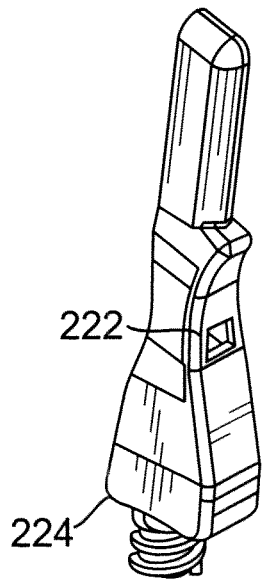
FIG. 19 is a rear/side perspective view of another embodiment of the present hinged shield assemblies in a protected position.

FIGS. 16-18 further illustrate the structure of the hub 106. With reference to FIG. 18, the proximal cylindrical portion 152 includes a female taper 178 on its interior that is configured to matingly receive a male tapered tip of the syringe 102 (FIG. 1). The distal cylindrical portion 154 also includes a female bore 180 on its interior that is configured to receive the proximal blunt end of the needle 104 (FIG. 4). The distal cylindrical portion 154 also includes a plurality of longitudinally spaced annular indentations 182 (FIG. 18) configured to receive annular ridges 184 (FIG. 4) on the needle 104. In an alternative embodiment, the cylindrical portion 154 has a male taper for projecting into a separately provided combination needle hub and needle. This alternative embodiment allows a practitioner to use any number of needle sizes with the hinged cap device.

FIGS. 1-4 illustrate the hinged shield assembly 100 in the assembled state. When the assembly 100 is manufactured, the shield 108 is assembled to the huh 106 by flexing the first and second sidewalls 110, 112 (FIGS. 2 and 3) away from each other in the area of the base end 116 of the shield 108. The slits 124 (FIGS. 5 and 6) between the first and second sidewalls 110, 112 and the third sidewall 114 facilitate the flexing. The shield 108 and hub 106 are then positioned such that the balls 134 are just outside the openings 168 (FIG. 15) in the sockets 142. The sidewalls 110, 112 are then forced inward so that the balls 134 squeeze through the narrower openings 168 and into the sockets 142. As these steps are performed, the shield 108 is positioned at an appropriate angle relative to the hub 106 so that the tabs 136 and/or sidewalls 110, 112 do not interfere with the hub 106. For example, the shield 108 and hub 106 may be positioned such that their longitudinal axes are perpendicular to one another.

Also when the assembly 100 is manufactured, it may be capped to safely cover the sharp distal tip 186 (FIG. 4) of the needle 104 prior to use. With reference to FIG. 4, the assembly 100 includes a tapered cylindrical cap 188 that fits over the distal cylindrical portion 154 of the hub 106 in a friction fit. An outer diameter of the cap 188 is sized so that the base end 116 of the shield 108 can extend around at least part of the cap 188, enabling the shield 108 to be pivoted toward the cap 188 as shown in FIG. 4. In this configuration the assembly 100 occupies less space for shipping as compared to a configuration in which the shield 108 extends perpendicularly to the cap 188.

To use the present hinged shield assembly 100, the operator typically begins with the assembly 100 in the capped configuration of FIG. 4. The operator pivots the shield 108 away from the cap 188 and removes the cap 188. The assembly 100 is then ready to be used to inject medication or to draw blood. Advantageously, the ball-and-socket hinge 144 enables the shield 108 to be retained at any desired angle with respect to the needle 104 without the need for the operator to hold the shield 108 in place. The operator's fingers are thus available to perform other tasks. As mentioned above, the relative sizes and/or shapes of the balls 134 and sockets 142 can be tailored to provide desired relative motion. For example, these components can be manufactured for an interference fit so that friction and interference between the moving parts retains the shield 108 at the desired angle after the operator releases the shield 108. Further examples of sizes and shapes of the balls 134 and sockets 142 are discussed below.

After the injection or blood draw, the operator pivots the shield 108 toward the needle 104 by applying manual force. The operator continues to pivot the shield 108 until the hooks 130 snap around the needle 104 and the tabs 136 snap into the notches 174. With the needle 104 safely surrounded by the shield 108 (FIG. 1), the assembly 100 is ready to be discarded.

FIGS. 8-11 illustrate alternative shapes for the outer surfaces of the balls 134. The alternative shapes are shown in conjunction with the spherical shape of FIGS. 5-7 to highlight the shape contrasts. With reference to FIG. 8, possible alternative shapes include various regular and irregular polyhedrons having a plurality of faces 190. Examples of regular polyhedrons include dodecahedron, icosahedron, octahedron, or any other polyhedron. Each of these shapes includes a plurality of faces 190 having congruent shapes. In an irregular polyhedron the faces 190 do not have congruent shapes, and the faces 190 may extend partially or fully around the circumference of the ball 134.

With reference to FIG. 9, another alternative shape provides a single face 192, or flat surface, that forms a plane extending perpendicularly to the first and second sidewalls 110, 112. A corresponding face (not shown) may be provided in the socket 142 so that when the shield 108 reaches a desired angle with respect to the needle 104, such as perpendicular, the face 192 on the ball 134 abuts the face on the socket to hold the shield 108 at the desired angle. There may be a second face 192 on the opposite side of the ball 134, in which case the socket would also include a second face positioned opposite the first face.

With reference to FIG. 10, another alternative shape provides a plurality of faces 194 that form planes extending perpendicularly to the first and second sidewalls 110, 112. The faces 194 may extend partially or fully around the circumference of the ball 134. Corresponding faces (not shown) may be provided in the socket 142 so that as the shield 108 pivots the faces 194 on the ball 134 sequentially abut the faces in the socket. The resulting motion provides a ratchet-like effect that enables the shield 108 to be held at a variety of different angles with respect to the needle 104.

With reference to FIG. 11, another alternative shape provides a single face 196 that forms a plane extending perpendicularly to the first and second sidewalls 110, 112. Comparing FIGS. 9 and 11, the faces 192, 196 have similar shapes. However, the face 192 of FIG. 9 has a long dimension extending parallel to the first and second sidewalls 110, 112, while face 196 of FIG. 11 has a long dimension extending perpendicular to the first and second sidewalls 110, 112. A corresponding face (not shown) may be provided in the socket 142 so that when the shield 108 reaches a desired angle with respect to the needle 104, such as perpendicular, the face 196 on the ball 134 abuts the face 196 on the socket 142 to hold the shield 108 at the desired angle. There may be a second face on the opposite side of the ball 134, in which case the socket 142 would also include a second face positioned opposite the first face 196.

While not illustrated, the balls 134 could have additional shapes. Example alternative shapes include disc, cube, cuboid, ellipsoid, egg-shaped, oval, or any other shape. The ball 134 could also include a slit so that it could compress while being inserted into the socket 142 for a snap fit. The sockets 142 could have shapes complementary to any of the foregoing shapes. The balls 134 and/or sockets 142 could include texturing, such as knurling. Also, while in the illustrated embodiments the balls 134 are on the shield 108 and the sockets 142 are on the hub 106, in alternative embodiments the balls 134 could be on the hub 106 and the sockets 142 on the shield 108. Also, while in the illustrated embodiment two balls 134 and two sockets 142 are provided, in alternative embodiments any number of balls 134 and sockets 142 could be provided.

The present embodiments may be constructed from suitable materials, such as plastics. Preferably, the plastics are medical grade plastics. The shield 108 and hub 106 may be injection molded as separate pieces and then secured to one another as described above. Example materials for the shield 108 and hub 106 include acrylonitrile butadiene styrene (ABS), polyethylene, polypropylene (PP), fluorinated ethylene propylene (FEP), polytetrafluoroethylene (PTFE), polychlorotrifluoroethylene (PCTFE), and others.

FIGS. 19-40 illustrate alternative embodiments of the present hinged shield assemblies. These alternative embodiments share many similarities with the embodiments described above and shown in FIGS. 1-18. Accordingly, the following discussion focuses on the features of FIGS. 19-40 that differ from the embodiments of FIGS. 1-18.

Figure 20:
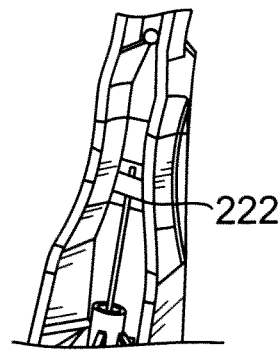
FIG. 20 is a front/side perspective view of a portion of the hinged shield assembly of FIG. 19, showing a needle-securing hook extending around the needle to hold the shield in the protected position.
Figure 21:
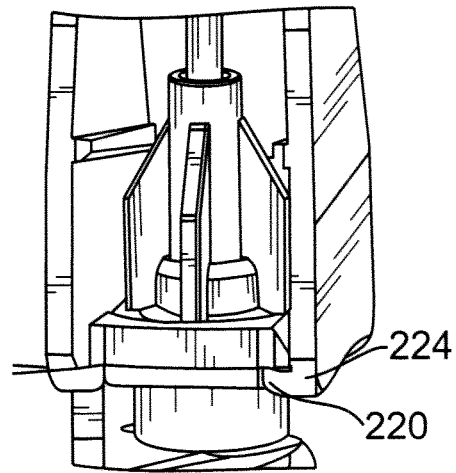
FIG. 21 is a front perspective view of another portion of the hinged shield assembly of FIG. 19, showing a shield lock on the needle hub and the shield holding the shield in the protected position.
Figure 22:
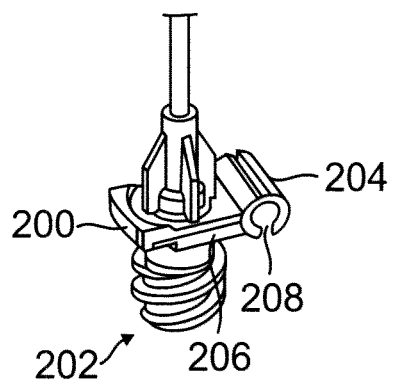
FIG. 22 is a side perspective view of the needle hub of the hinged shield assembly of FIG. 19.

FIGS. 19-23 illustrate one alternative embodiment in which the ball-and-socket hinge is replaced with a bar-and-channel hinge. With reference to FIG. 22, the transverse base 200 of the hub 202 includes a channel 204 formed as a partial hollow cylinder. The channel 204 adjoins the substantially planar portion 206 of the transverse base 200 such that a longitudinal axis of the channel 204 extends perpendicularly to an axis of the needle 104 and lies in or near a plane formed by the substantially planar portion 206. The channel 204 is open at both ends and includes a narrow opening 208 that extends along its proximal side.

Figure 23:
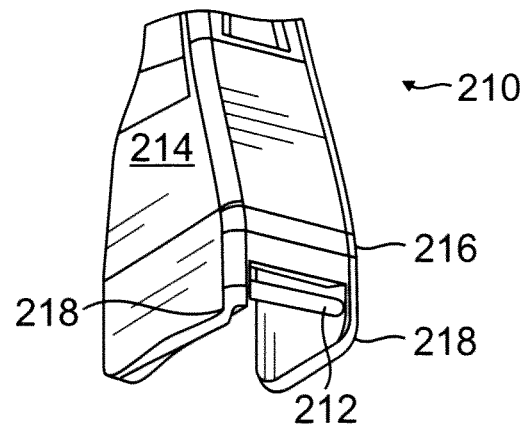
FIG. 23 is a rear/side perspective view of the shield of the hinged shield assembly of FIG. 19.

With reference to FIG. 23, the shield 210 includes a cylindrical bar 212 that extends between the first and second sidewalls 214, 216 near opposing corners 218 thereof. The bar 212 is sized to be received in the channel 204 in a snug fit or interference fit so that the shield 210 can be held at a desired pivot angle with respect to the hub 202, as discussed above. To assemble the shield 210 to the hub 202, the bar 212 is forced into the channel 204 through the opening 208. The channel 204 is configured to flex so that the width of the opening 208 can increase temporarily to allow the bar 212 to pass. Once the bar 212 passes, the channel 204 returns to its original shape in order to provide a snug fit or interference fit with the bar 212. As the assembly steps are performed, the shield 210 is positioned at an appropriate angle relative to the hub 202 so that the tabs 220 (FIG. 21) and/or sidewalls 214, 216 do not interfere with the hub 202. For example, the shield 210 and the hub 202 may be positioned such that their longitudinal axes are perpendicular to one another.

Figure 24:
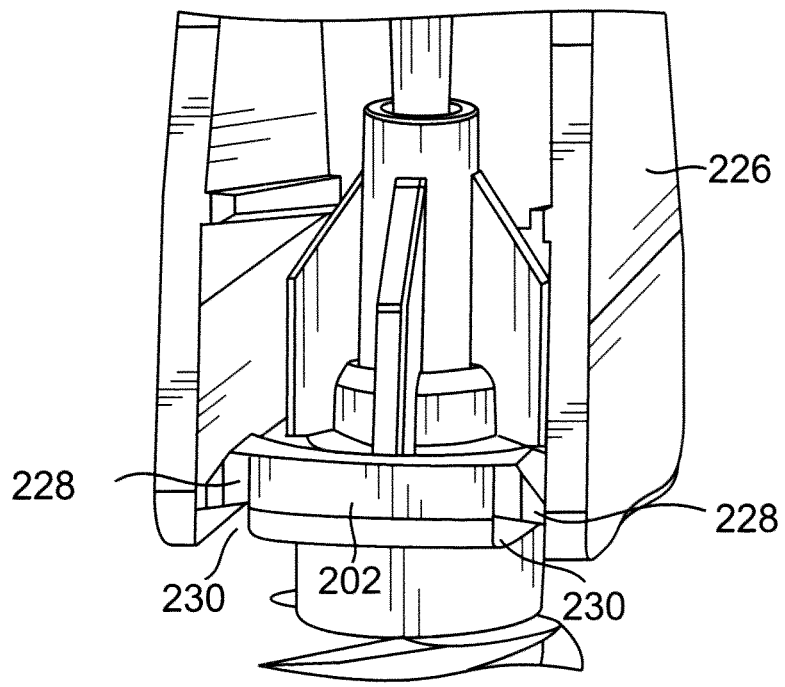
FIG. 24 is a front perspective view of an alternative configuration of the hinged shield assembly of FIG. 21 in which the shield lock on the needle hub and the shield is eliminated.

With reference to FIGS. 20 and 21, the embodiment of FIGS. 19-23 includes both the hook 222 and the reversible shield lock 224. FIG. 24 illustrates an alternative to the embodiment of FIGS. 19-23 in which the reversible shield lock is omitted. As illustrated, the shield 226 does not include the first and second tabs that are present in the embodiment of FIG. 21. Thus, when the shield 226 is in the needle-protected position, there is no structure on the shield 226 to interlock with the ledges 228 and notches 230 on the hub 202.

Figure 26:
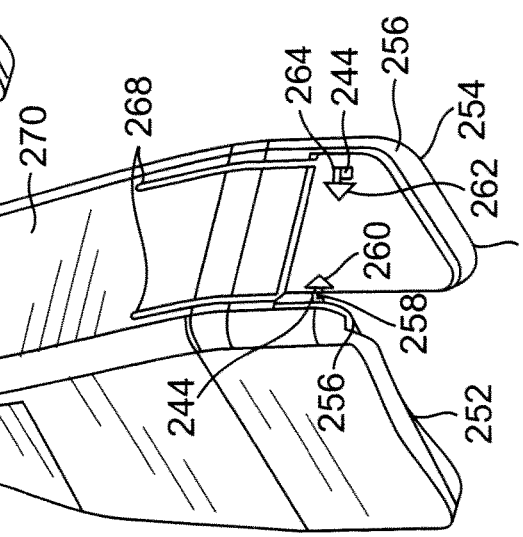
FIG. 26 is a lower/rear perspective view of an alternative configuration of a shield of the present hinged shield assemblies, the shield being compatible with the hub of FIG. 25.
Figure 25:
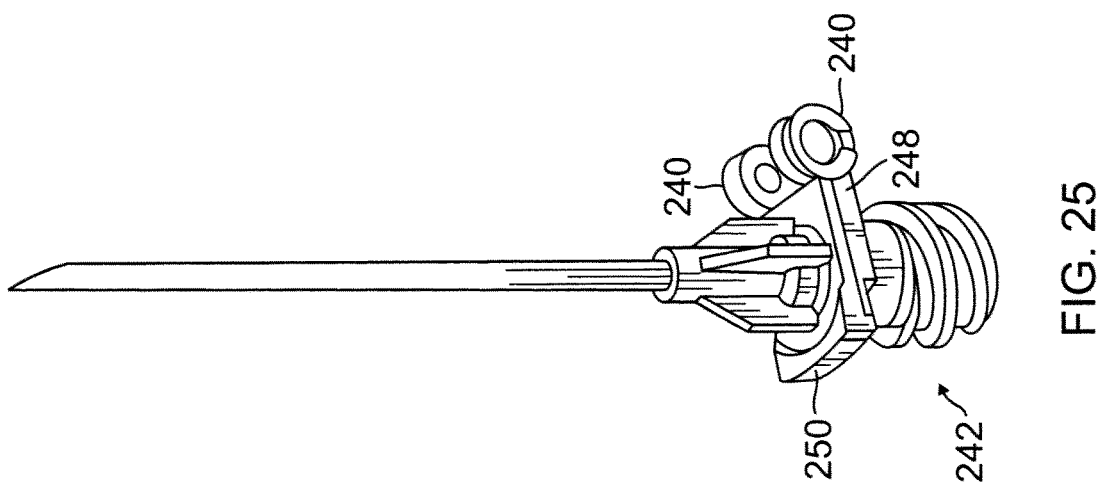
FIG. 25 is a side perspective view of an alternative configuration of a needle hub of the present hinged shield assemblies.

FIGS. 25 and 26 illustrate another alternative embodiment in which the hinge comprises first and second rings 240 on the hub 242 that receive first and second posts 244 on the shield 246. With reference to FIG. 25, the first and second rings 240 are spaced from one another and adjoin the substantially planar portion 248 of the transverse base 250 such that a longitudinal axis passing through both rings 240 lies in or near a plane formed by the substantially planar portion 248.

With reference to FIG. 26, the shield 246 includes the first and second posts 244 that extend inward from the first and second sidewalls 252, 254 near opposing corners 256 thereof. The posts 244 are spaced from one another. Each post 244 includes a cylindrical portion 258 adjoining its respective sidewall 252, 254 and a conical cap portion 260 at the end of the cylindrical portion 258 and spaced from the respective sidewall 252, 254. The caps 260 are arranged so that the tapered surface 262 of each faces away from its respective cylindrical portion 258. A flat surface of each cap thus forms a transverse annular shoulder 264 about its respective cylindrical portion 258.

The cylindrical portions 258 are sized to be received in respective ones of the rings 240 in a snug fit or interference fit so that the shield 246 can be held at a desired pivot angle with respect to the hub 242, as discussed above. The conical caps 160 vary in diameter from the vertex of each to a maximum diameter at the base of each. The maximum diameter is greater than the interior diameter of each ring 240. Thus, when the shield 246 is assembled to the hub 242 the caps 260 resist withdrawal of the posts 244 from the rings 240.

To assemble the shield 246 to the hub 242, the first and second sidewalls 252, 254 are flexed away from each other in the area of the base end 266 of the shield 246. The slits 268 between the first and second sidewalls 252, 254 and the third sidewall 270 facilitate the flexing. The shield 246 and hub 242 are then positioned such that the posts 244 are just lateral of the openings in the rings 240. The sidewalls 252, 254 are then forced inward so that the caps 260 squeeze through the rings 240 until the maximum diameter portion of each cap 260 is positioned medially of the rings 240. The transverse annular shoulders 264 of the caps 260 abut the rings 240 to resist withdrawal. While not visible in FIG. 26, each of the caps 260 includes a slit that bisects the cap 260. The slit enables the halves of the cap 260 to flex toward one another to enable the cap 260 to squeeze through its respective ring 240. When the maximum diameter portion of the cap 260 passes through the ring 240 the halves of the cap 260 snap back to the unstressed configuration. As the assembly steps are performed, the shield 246 is positioned at an appropriate angle relative to the hub 242 so that the sidewalls 252, 254 do not interfere with the hub 242. For example, the shield 246 and hub 242 may be positioned such that their longitudinal axes are perpendicular to one another.

Figure 27:
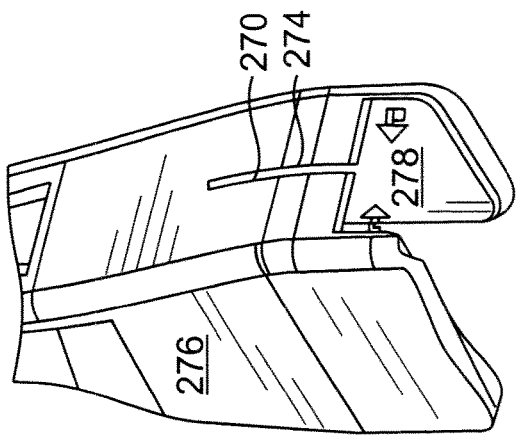
FIG. 27 is a lower/rear perspective view of an alternative configuration of a shield of the present hinged shield assemblies, the shield being compatible with the hub of FIG. 25.

FIG. 27 illustrates an alternative configuration for the shield 246 of FIG. 26, in which the dual slits 268 are replaced with a single slit 272 that extends through the third sidewall 274 at a location evenly spaced from the first and second sidewalls 276, 278. The slit 272 facilitates flexing of the first and second sidewalls 276, 278 away from one another. The third sidewall 274 may alternatively be referred to as the center wall, which is located between the two sidewalls of the generally U-shape cap.

Figure 28:
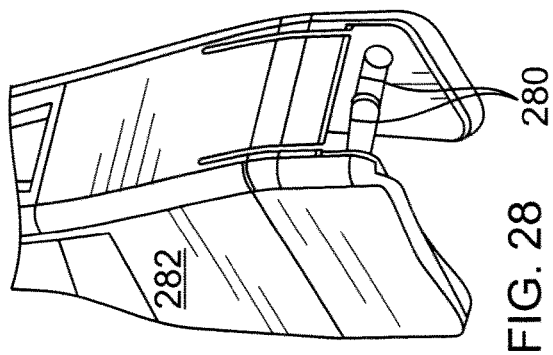
FIG. 28 is a lower/rear perspective view of an alternative configuration of a shield of the present hinged shield assemblies, the shield being compatible with the hub of FIG. 25.

FIG. 28 illustrates another alternative configuration for the shield 246 of FIG. 26, in which the posts 280 have a different size and shape. In the embodiment of FIG. 28, each post 280 is cylindrical; the caps or hoods 260 at the ends of the posts of FIG. 26 are omitted. Further, the posts 280 abut one another or are spaced only slightly from one another. The additional length of each post 280 compensates for the omitted caps 260 in retaining the posts 280 within the rings 240. For further security against the posts 280 withdrawing from the rings 240, the ends of the posts 280 may be secured to one another by, for example, adhesive or welding after the shield 282 and hub 242 are mounted to one another.

Figure 30:
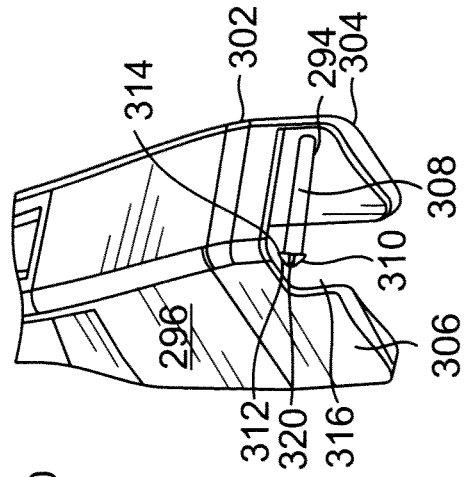
FIG. 30 is a lower/rear perspective view of an alternative configuration of a shield of the present hinged shield assemblies, the shield being compatible with the hub of FIG. 29.
Figure 29:
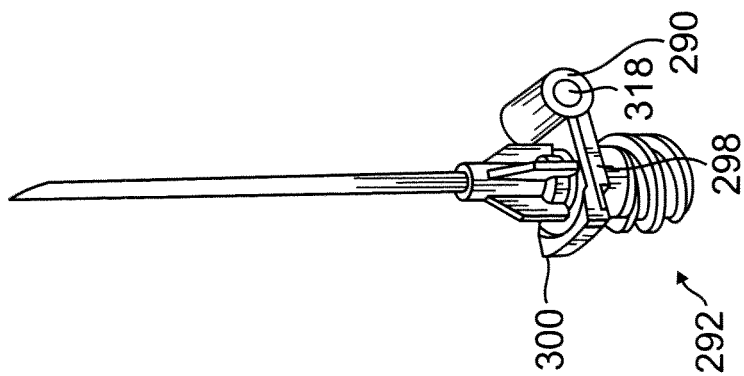
FIG. 29 is a side perspective view of an alternative configuration of a needle hub of the present hinged shield assemblies.

FIGS. 29 and 30 illustrate another alternative embodiment in which the hinge comprises a cylinder 290 on the hub 292 that receives a single post 294 on the shield 296. With reference to FIG. 29, the cylinder 290 has a closed sidewall and is open at either end. The cylinder 290 adjoins the substantially planar portion 298 of the transverse base 300 such that a longitudinal axis passing through the cylinder 290 lies in or near a plane formed by the substantially planar portion 298.

With reference to FIG. 30, the shield 296 includes the single post 294 that extends inward from the first sidewall 302 near a corner 304 thereof. The post 294 extends to, or almost to, a plane defined by the second sidewall 306. The post 294 includes a cylindrical portion 308 adjoining the first sidewall 302 and a conical cap portion 310 at the end of the cylindrical portion 308 and spaced from the first sidewall 302. The cap 310 is arranged so that its tapered surface 312 faces away from the cylindrical portion 308. A flat surface of the cap 310 thus forms a transverse annular shoulder 314 about the cylindrical portion 308.

The cylindrical portion 308 is sized to be received in the cylinder 290 in a snug fit or interference fit so that the shield 296 can be held at a desired pivot angle with respect to the hub 292, as discussed above. The cap 310 varies in diameter from its vertex to a maximum diameter at its base. The maximum diameter is greater than the interior diameter of the cylinder 290. Thus, when the shield 296 is assembled to the hub 292 the cap 310 resists withdrawal of the post 294 from the cylinder 290.

With reference to FIG. 30, the shield 296 further includes a rectangular cutout 316 at a corner of the second sidewall 306 opposite the corner 304 of the first sidewall 302 from which the post 294 extends. Due to the length of the post 294 and the length of the cylinder 290, it would be difficult to flex the first and second sidewalls 302, 306 away from one another sufficiently to enable the post 294 to be slid into the cylinder 290. The cutout 316 thus accommodates the cylinder 290 when the shield 296 is mounted to the hub 292, as described below.

To assemble the shield 296 to the hub 292, the shield 296 is positioned laterally of the hub 292 so that the cap 310 on the post 294 is positioned just laterally of the opening 318 in the cylinder 290, and such that an angle defined between the longitudinal axes of the shield 296 and the hub 292 is between approximately 90° and approximately 180°. This range of angles enables the cutout 316 in the second sidewall 306 to accommodate the hub 292 as the shield 296 and hub 292 are moved laterally toward one another. As the shield 296 and hub 292 are moved laterally toward one another, the cap 310 squeezes through the interior of the cylinder 290 until the maximum diameter portion of the cap 310 reaches the opposite side. The transverse annular shoulder 314 of the cap 310 abuts the cylinder 290 to resist withdrawal. As shown, the cap 310 includes a slit 320 that bisects the cap 310. The slit 320 enables the halves of the cap 310 to flex toward one another to enable the cap 310 to squeeze through the cylinder 290. When the maximum diameter portion of the cap 310 passes through the cylinder 290 the halves of the cap 310 snap back to the unstressed configuration.

Figure 31:
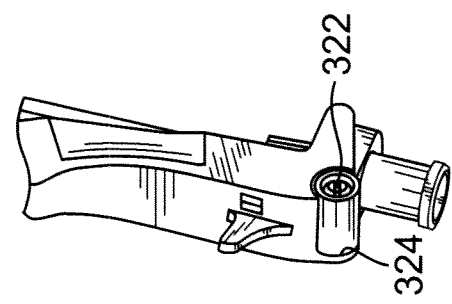
FIG. 31 is a lower/rear perspective view of an assembly including a needle hub similar to that of FIG. 29 and a shield similar to that of FIG. 30.

FIG. 31 illustrates an alternative embodiment to that of FIGS. 29 and 30 but having a similar hinge. As shown, the cap 322 extends to the far side of the cylinder 324 such that the transverse annular shoulder (not shown) bears against the cylinder 324 to resist withdrawal of the post from the cylinder 324.

Figure 32:
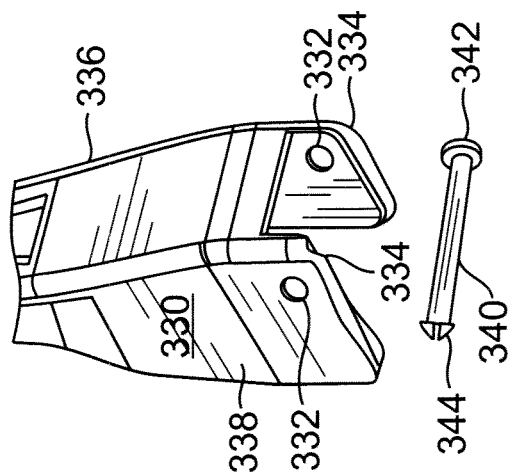
FIG. 32 is a lower/rear perspective view of an alternative configuration of a shield of the present hinged shield assemblies, the shield being compatible with the hub of FIG. 29.

FIG. 32 illustrates an alternative shield 330 having a hinge part compatible with the cylinder 290 of FIG. 29. The shield 330 of FIG. 32 does not include the cutout 316 that the shield 296 of FIG. 30 does. Instead, the shield 330 includes first and second apertures positioned at opposing corners 334 of the first and second sidewalls 336, 338. The shield 330 further comprises a post 340 that is a discrete piece from the first and second sidewalls 336, 338. The post 340 is cylindrical and includes a constant diameter, except for an enlarged diameter flat head 342 at a first end, and a second end shaped as a cap 344 analogous to the cap 310 of FIG. 30.

To mount the shield 330 of FIG. 32 to the hub 292 of FIG. 29, the shield 330 is positioned so that the first and second sidewalls 336, 338 surround the cylinder 290 at either end and the apertures 332 are coaxial with the cylinder 290. The post 340 is then inserted, cap end 344 first, through the first sidewall 336, through the cylinder 290, and finally through the second sidewall 338 until the cap 344 protrudes from the second sidewall 338. The diameters of the head 342 and the cap 344 are each greater than the diameters of the apertures 332 so that the post 340 resists withdrawal from the apertures 332.

Figure 33:
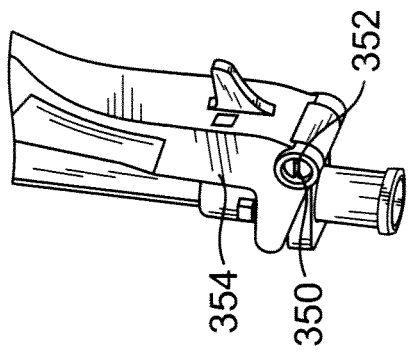
FIG. 33 is a lower/rear perspective view of an assembly including a needle hub similar to that of FIG. 29 and a shield similar to that of FIG. 32.

FIG. 33 illustrates an alternative embodiment to that of FIGS. 29 and 32 but having a similar hinge. As shown, the cap 350 extends through the aperture 352 in the second sidewall 354 and the transverse annular shoulder (not shown) bears against the sidewall 354 to resist withdrawal of the post from the aperture 352.

FIGS. 34 and 36 illustrate an alternative embodiment similar to that of FIGS. 25 and 26, except that the locations of the posts and openings are reversed. With reference to FIG. 34, the hub 360 includes a cylinder 362 that is located and oriented similarly to the cylinder 290 of FIG. 29. The cylinder 362, however, is solid, or at least closed at both ends. First and second posts 364 extend outwardly in opposite directions from the ends of the cylinder 362. The posts 364 are substantially identical to the posts 244 of FIG. 26, except for their location and opposite orientation. The shield 366 of FIG. 36 is substantially identical to the shield 330 of FIG. 32, including first and second apertures 368 positioned at opposing corners 370 of the first and second sidewalls 372, 374. However, the shield 366 of FIG. 36 includes first and second slits 376 analogous to the slits 268 of FIG. 26. The process for mounting the shield 366 of FIG. 36 on the hub 360 of FIG. 34 is substantially identical to the process for mounting the shield 246 of FIG. 26 on the hub 242 of FIG. 25, described above, except that the posts 364 on the hub 360 (FIG. 34) are forced through the apertures 368 on the first and second sidewalls 372, 374 (FIG. 36), rather than the posts 244 on the first and second sidewalls 252, 254 (FIG. 26) being forced through the rings 240 (FIG. 25).

FIG. 37 illustrates an alternative embodiment to that of FIGS. 34 and 36 but having a similar hinge. As shown, the caps 380 on the posts (not shown) extend through the apertures 382 in the sidewalls 384, 386 and the transverse annular shoulders (not shown) bear against the sidewalls 384, 386 to resist withdrawal of the posts from the apertures 382.

FIG. 35 illustrates an alternative embodiment to the hub 360 of FIG. 34. In FIG. 35 the cylinder 362 of FIG. 34 is replaced with first and second tabs 390. Each tab 390 is shaped substantially as a triangle and defines a plane extending perpendicularly to that of the substantially planar portion 392. One vertex of each triangle abuts the substantially planar portion 392 so that the height of each tab 390 increases with increasing distance from the substantially planar portion 392. The posts 394 extend outwardly in opposite directions from the tabs 392.

Figure 38:
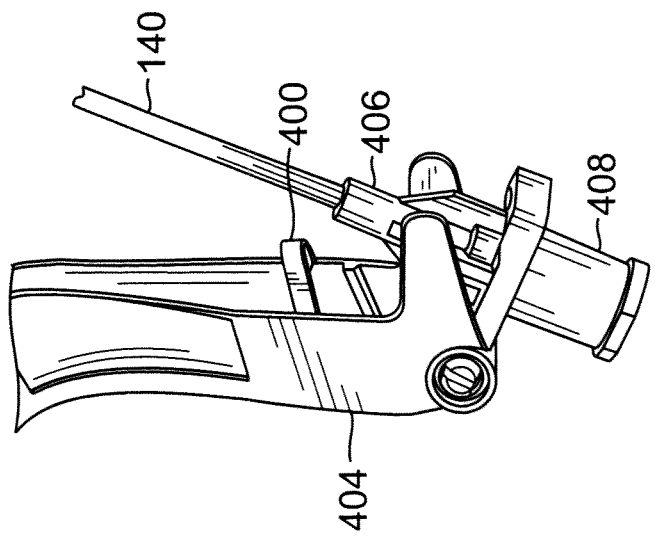
FIG. 38 is a side perspective view of another embodiment of the present hinged shield assemblies.
Figure 39:
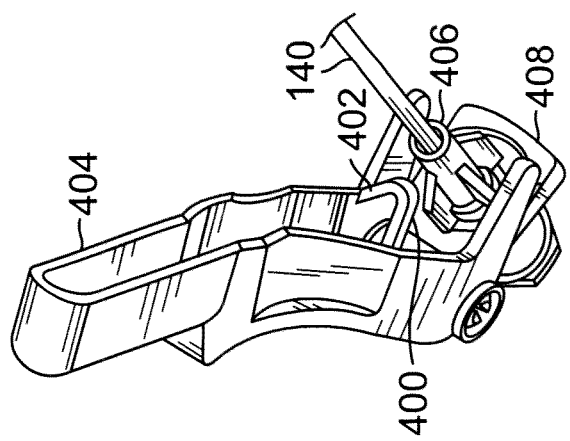
FIG. 39 is an upper/side perspective view of the hinged shield assembly of FIG. 38.
Figure 40:
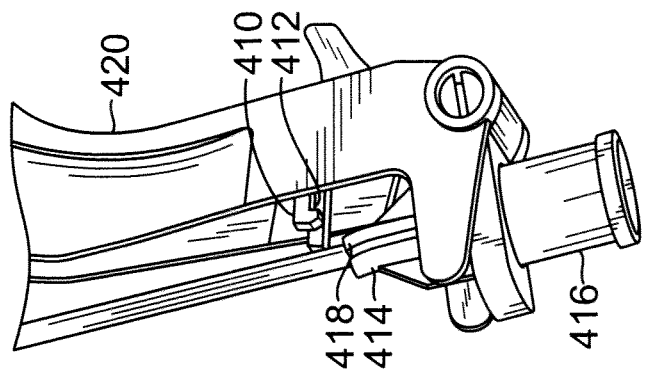
FIG. 40 is a lower/side perspective view of an alternative configuration of the hinged shield assembly of FIG. 38 showing a different hook.

FIGS. 38-40 illustrate alternative configurations for the hook that secures the shield in the needle-protected position. With reference to FIGS. 38 and 39, the hook 400 includes a crook portion 402 (FIG. 39) that extends laterally. Also, the hook 400 is located on the shield 404 at a location so that when the shield 404 reaches the needle-protected position the hook 400 engages the distal cylindrical portion 406 of the hub 408, rather than the needle 140 as in the previous embodiments. With reference to FIG. 40, the hook 410 includes a crook portion 412 that extends proximally. The distal cylindrical portion 414 of the hub 416 includes a fin 418 that extends longitudinally a sufficient distance so that when the shield 420 reaches the needle-protected position the hook 410 engages the fin 418.

The above description presents the best mode contemplated for carrying out the present hinged shield assemblies, and of the manner and process of making and using them, in such full, clear, concise, and exact terms as to enable any person skilled in the art to which they pertains to make and use these hinged shield assemblies. These hinged shield assemblies are, however, susceptible to modifications and alternate constructions from that discussed above that are fully equivalent. Consequently, these hinged shield assemblies are not limited to the particular embodiments disclosed. On the contrary, these hinged shield assemblies cover all modifications and alternate constructions coming within the spirit and scope of the hinged shield assemblies as generally expressed by the following claims, which particularly point out and distinctly claim the subject matter of the hinged shield assemblies.

What is claimed is:

1. A hinged shield assembly configured to shield a needle to prevent needlesticks, the assembly comprising:

a needle hub including a first hinge part defining a first socket and a second socket, the needle extending from the needle hub; and a shield including a second hinge part defining a first ball and a second ball, the first ball and the second ball engaging the first socket and the second socket to pivotably secure the shield to the needle hub, the shield further including a plurality of side walls configured to partially surround the needle when the shield assembly is in a protected position, the plurality of side walls including a center wall located between a first side wall having the first ball located thereon and a second side wall having the second ball located thereon;

wherein each of the first socket and the second socket comprises an opening with a diameter that increases inward of the opening to a maximum diameter then tapers down to a narrower diameter that is smaller than the maximum diameter and wherein each ball has a diameter that is greater than the diameter of the opening so that the first ball and the second ball seat within the first socket and the second socket and resist withdrawal from the first socket and the second socket.

2. The hinged shield assembly of claim 1, wherein the shield comprises a base at a proximal end and wherein a slit is provided at the base between the first side wall and the center wall and a slit is provided at the base between the second side wall and the center wall, the two slits enabling the first and second side walls to bend away from one another to facilitate mounting the shield to the needle hub.

3. The hinged shield assembly of claim 1, wherein the first and second balls and the first and second sockets are arranged in an interference fit to provide a desired amount of resistance to rotation of the first and second balls within the first and second sockets.

4. The hinged shield assembly of claim 1, wherein the needle hub further comprises a first part of a shield lock located on a transverse base portion opposite the first hinge part and the shield further comprises a second part of the shield lock.

5. The hinged shield assembly of claim 4, wherein the shield lock is reversible and deflectable by bending the first side wall and the second side wall.

6. The hinged shield assembly of claim 4, wherein the transverse base portion comprises a ledge having a ramped first surface and forming a notch adjacent a second surface opposite the first surface.

7. The hinged shield assembly of claim 1, wherein the first ball extends inwardly from an inner surface of the first side wall and second ball extends inwardly from an inner surface of the second sidewall.

8. A method of making a hinged shield assembly configured to shield a needle to prevent needlesticks, the assembly including a needle hub and a shield comprising a plurality of side walls configured to partially surround the needle when the shield assembly is in a protected position, the plurality of side walls comprising a center wall located between a first side wall and a second side wall, the method comprising:

forming the needle hub with a base portion that is transverse to an axis defined by the needle, said base portion having a cylindrical portion having a first hinge part with a first socket and a second socket and extending the needle from the needle hub;

forming the shield with a second hinge part having a first ball on the first side wall and a second ball on the second side wall; and engaging the first hinge part and the second hinge part with one another by engaging the first ball with the first socket and the second ball with the second socket to pivotably secure the shield to the needle hub;

wherein each of the first socket and the second socket comprises an opening with a diameter that increases inward of the opening to a maximum diameter then tapers down to a narrower diameter that is smaller than the maximum diameter and wherein each ball has a diameter that is greater than the diameter of the opening so that the first ball and the second ball seat within the first socket and the second socket and resist withdrawal from the first socket and the second socket.

9. A method of using a hinged shield assembly to shield a needle to prevent needlesticks, the assembly including a needle hub and a shield, the shield has a plurality of side walls including a center wall located between first and second sidewalls, the method comprising:

pivoting the shield with respect to the needle hub about a hinge that pivotably secures the shield to the needle hub;

continuing to pivot the shield with respect to the needle hub until the side walls partially surround the needle in a protected position;

locking the shield with respect to the needle hub by engaging a first tab on the shield with a first notch on a transverse base portion on the needle hub and a second tab on the shield with a second notch on the transverse base portion of the needle hub;

wherein pivoting the shield with respect to the needle hub about the hinge comprises pivoting a first ball within a first socket and pivoting a second ball within a second socket, the first and second sockets located on the transverse base portion, and wherein the first ball and the first socket and the second ball and the second socket are in interference fit such that the shield remains at any desired angle relative to the needle when the shield pivots within a range of angles relative to the needle hub; and wherein each of the first socket and the second socket comprises an opening with a diameter that increases inward of the opening to a maximum diameter then tapers down to a narrower diameter that is smaller than the maximum diameter and wherein each ball has a diameter that is greater than the diameter of the opening so that the first ball and the second ball seat within the first socket and the second socket and resist withdrawal from the first socket and the second socket.

10. The hinged shield assembly of claim 1, wherein the first ball and the second ball are spaced from one another by a gap and wherein the first ball and the second ball each comprises a planar surface formed thereon.

11. The hinged shield assembly of claim 4, wherein the first socket and the second socket are located on a first side edge of the transverse base portion and a first notch and a second notch for engaging a first tab and a second tab of the shield are located on a second side edge of the transverse base portion.

12. The method of claim 9, wherein the first ball is attached to an inside surface of the first side wall and the second ball is attached to an inside surface of the second side wall.

13. The hinged shield assembly of claim 4, wherein a hook extends from the center wall and is sized and shaped to hook onto the needle in a protected position.

14. The method of claim 8, wherein the first socket and the second socket share a common bore and wherein the first ball and the second ball are connected at two ends of the common bore.

15. The method of claim 8, further comprising a first tab extending from the first side wall at a corner opposite the first ball and a second tab extending from the second side wall at a corner opposite the second ball to engage notches formed on the base portion of the needle hub in the protected position.

16. The method of claim 8, further comprising rotating the shield to a first position away from the needle, and wherein the shield is held in the first position by interference between the first ball and the first socket and the second ball and the second socket.

17. The method of claim 8, wherein the shield comprises a base at a proximal end and wherein a slit is provided at the base between the first side wall and the center wall and a slit is provided at the base between the second side wall and the center wall, the two slits enabling the first and second side walls to bend away from one another to facilitate engaging the first and second balls on the shield with the first and second sockets on the needle hub.

18. The method of claim 9, wherein the first ball and the second ball are spaced from one another by a gap and wherein the first ball and the second ball each comprises a planar surface formed thereon.

19. The method of claim 9, wherein locking the shield to the needle hub further comprises locking a hook formed with the center wall to the needle.

20. The method of claim 9, wherein the first tab extends from the first side wall and the second tab extends from the second side wall at locations on the first and second side walls opposite the first ball and the second ball.

21. The method of claim 20, wherein the transverse base portion comprises ramped surfaces for deflecting the first and second tabs as the shield rotates over the needle.

22. A hinged shield assembly configured to shield a needle to prevent needlesticks, the assembly comprising:
    a needle hub comprising base portion that is transverse to a lengthwise axis of the needle hub, the base portion having a first hinge part with a first socket and a second socket located along a first side of the base portion and a first notch and a second notch located on a second side of the base portion, the needle extending from the needle hub; and
    a shield including a second hinge part defining a first ball and a second ball, the first ball and the second ball engaging the first socket and the second socket to pivotably secure the shield to the needle hub, the shield further including a plurality of side walls configured to partially surround the needle when the shield assembly is in a protected position and the shield is in a closed configuration and the shield being rotatable away from the needle until physically stopped in a fully opened configuration, the plurality of walls including a center wall located between a first side wall having the first ball and a second side wall having the second ball, the plurality of side walls including a first slit between the first side wall and the center wall and a second slit between the second side wall and the center wall;
    wherein each of the first socket and the second socket comprises an opening with a diameter that increases inward of the opening to a maximum diameter then tapers down to a narrower diameter that is smaller than the maximum diameter and wherein each ball has a diameter that is greater than the diameter of the opening so that the first ball and the second ball seat within the first socket and the second socket and resist withdrawal from the first socket and the second socket.

23. The hinged shield assembly of claim 22, further comprising a first tab on the first side wall and a second tab on the second side wall, the first tab and the second tab engaging the first notch and the second notch in the closed configuration.

24. The hinged shield assembly of claim 23, wherein the shield further comprises a hook formed with the center wall for locking onto the needle.

25. The hinged shield assembly of claim 24, wherein each ball comprises plurality of planar surfaces to provide a ratchet effect.

26. The hinged shield assembly of claim 25, wherein the base portion comprises ramped surfaces for deflecting the first and second tabs as the shield rotates over the needle.

27. The hinged shield assembly of claim 5, further comprising a cylindrical portion located on the transverse base portion and wherein the first socket is located on a first end of the cylindrical portion and the second socket is located on a second end of the cylindrical portion.

\* \* \* \* \*